(12) United States Patent
Fukuda et al.

(10) Patent No.: US 6,706,664 B1
(45) Date of Patent: Mar. 16, 2004

(54) BENZOXAZOLE COMPOUNDS, PROCESS FOR THE PREPARATION THEREOF AND HERBICIDES

(75) Inventors: Shohei Fukuda, Ube (JP); Akira Nakamura, Ube (JP); Motohisa Shimizu, Ube (JP); Tatsuo Okada, Ube (JP); Takehiko Asahara, Ube (JP); Satoshi Oohida, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/959,544

(22) PCT Filed: Apr. 27, 2000

(86) PCT No.: PCT/JP00/02760

§ 371 (c)(1),
(2), (4) Date: Oct. 30, 2001

(87) PCT Pub. No.: WO00/66569

PCT Pub. Date: Nov. 9, 2000

(30) Foreign Application Priority Data

Apr. 30, 1999 (JP) ............................................. 11-124912

(51) Int. Cl.$^7$ ........................ A01N 43/76; C07D 263/54
(52) U.S. Cl. ........................ 504/270; 548/217; 548/237
(58) Field of Search ........................ 504/270; 548/217, 548/237

(56) References Cited

U.S. PATENT DOCUMENTS

| | | |
|---|---|---|
| 2,423,730 A | 7/1947 | Salminen et al. |
| 2,478,366 A | 8/1949 | Brooker et al. |
| 2,801,171 A | 7/1957 | Fierke et al. |
| 3,582,322 A | 6/1971 | Edens et al. |
| 3,737,318 A | 6/1973 | Inoue et al. |
| 4,684,602 A | 8/1987 | Lelental et al. |
| 5,091,296 A | 2/1992 | Bagchi et al. |

FOREIGN PATENT DOCUMENTS

| | | |
|---|---|---|
| EP | 0 795 550 A1 | 8/1997 |
| EP | A1 0 795 550 | 8/1997 |
| GB | 1510545 | 5/1978 |
| JP | 10-319542 | 5/1997 |

OTHER PUBLICATIONS

G. Beck et al., Chemische Berichte, vol. 106, No. 9, pp. 2758–2766, 1973.

Cranham, et al., Journal of the Science of Food and Agriculture, pp. 143–147, Mar. 9, 1958.

G. Cohn, Journal Fur Praktishche Chemie, vol. 64, pp. 293–296, 1901.

Totton et al, Journal of the American Chemical Society, vol. 76, No. 20, pp. 5127–5128, Oct. 20, 1954.

Beilstein Registry No. 2868694 and J. Org. Chem. USSR (Engl. Transl.) vol. 1, pp. 2243, 1965.

Makosza et al., Tetrahedron, vol. 51, No. 26, pp. 7277–7286 (1995).

Musser et al., J. Med. Chem., vol. 30, pp. 400–405 (1987).

Oren et al., Drug. Res., vol. 47, No. 12, pp. 1393–1397 (1997).

Kim et al., Heterocycles, vol. 41, No. 4, pp. 641–646 (1995).

Yalcin et al., Il Farmaco, vol. 52, No. 11, pp. 685–689 (1987).

Primary Examiner—Alan L. Rotman
Assistant Examiner—Golamm M M Shameem
(74) Attorney, Agent, or Firm—Birch, Stewart, Kolasch & Birch, LLP

(57) ABSTRACT

The present invention relates to a benzoxazole compound represented by the following formula (1):

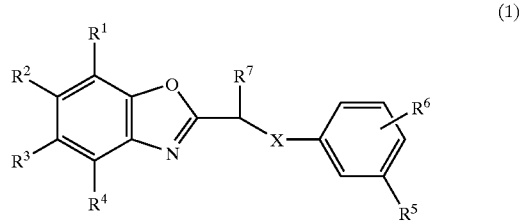

(1)

wherein $R^1$ to $R^4$ each represents hydrogen atom, $C_{1-6}$ alkyl group, $C_{1-4}$ alkoxy group, $C_{1-4}$ haloalkyl group, $C_{1-4}$ haloalkoxy group, halogen atom, nitro group, cyano group, etc.; $R^5$ represents $C_{1-4}$ haloalkyl group, $C_{1-4}$ haloalkoxy group, halogen atom, nitro group, cyano group, etc.; $R^6$ represents hydrogen atom, halogen atom, cyano group, nitro group, etc.; $R^7$ represents hydrogen atom, $C_{1-6}$ alkyl group, $C_{1-4}$ haloalkyl group, etc.; and X represents O, S, SO or $SO_2$, a process for producing the same and a herbicide containing the same as an effective ingredient.

13 Claims, No Drawings

BENZOXAZOLE COMPOUNDS, PROCESS FOR THE PREPARATION THEREOF AND HERBICIDES

This application is the national phase under 35 U.S.C. §371 of PCT International Application No. PCT/JP00/02760 which has an International filing date of Apr. 27, 2000, which designated the United States of America.

TECHNICAL FIELD

The present invention relates to a benzoxazole compound, a process for producing the same and a herbicide containing the same as an effective ingredient.

BACKGROUND ART

As a similar compound to a compound (1) according to the present invention, there is a compound represented by the following formula:

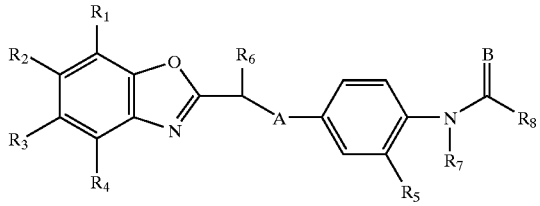

wherein $R_1$ to $R_6$ each represents a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom or a nitro group; A and B each represents O or S; $R_7$ represents a hydrogen atom, an alkyl group having 1 to 6 carbon atoms, etc.; and $R_8$ represents an alkyl group having 1 to 6 carbon atoms, etc., as disclosed in Japanese Provisional Patent Publication No. 139767/1998.

However, this compound is a compound different in at least —$NR^8CBR^9$ portion from the compound of the present invention.

Accordingly, since the compound (1) of the present invention is novel, its use has never been known. Also, a compound (6) which is a synthetic intermediate thereof is also a novel compound.

An object of the present invention is to provide a herbicide containing a benzoxazole compound as an effective ingredient.

SUMMARY OF THE INVENTION

The present inventors have earnestly investigated to solve the above-mentioned problems, and as a result, they have found that a chemical containing a novel benzoxazole derivative as an effective ingredient is effective as a herbicide whereby they have accomplished the present invention.

That is, the present invention is as follows:

The first invention relates to a benzoxazole compound represented by the following formula (1):

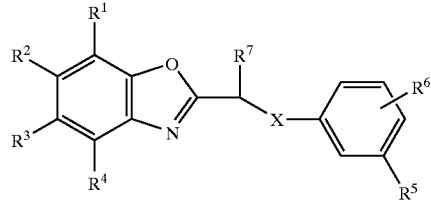

(1)

wherein $R^1$ to $R^4$ each represents a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, a carboxyl group, an alkoxycarbonyl group having 2 to 5 carbon atoms, $R^8S(O)_n$ or $R^9NH$ group; $R^8$ represents an alkyl group having 1 to 6 carbon atoms; n is an integer of 0 to 2; $R^9$ represents a hydrogen atom, an alkyl group having 1 to 4 carbon atoms, an alkylcarbonyl group having 2 to 4 carbon atoms; or a trifluoromethylcarbonyl group; $R^5$ represents a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group or $R^8S(O)_n$; $R^8$ has the same meaning as defined above; $R^6$ represents a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms; $R^7$ represents a hydrogen atom, an alkyl group having 1 to 6 carbon atoms, a haloalkyl group having 1 to 4 carbon atoms or a phenyl group; and X represents O, S, SO or $SO_2$.

The second invention relates to a process for preparing a compound (1') represented by the following formula (1') where X in the formula (1) is an oxygen atom or a sulfur atom:

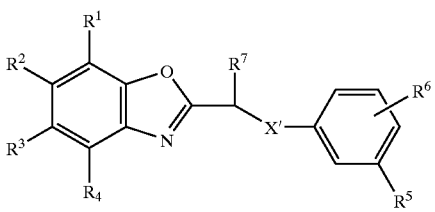

(1')

wherein $R^1$ to $R^7$ have the same meanings as defined above; and X' represents an oxygen atom or a sulfur atom, which comprises allowing a compound (2) represented by the following formula (2):

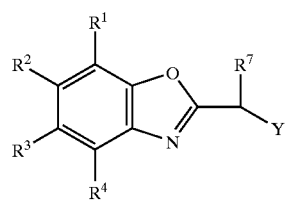

(2)

wherein $R^1$ to $R^4$ and $R^7$ have the same meanings as defined above; and Y represents a halogen atom, a methanesulfonyloxy group or a p-toluenesulfonyloxy group, to react with a compound represented by the following formula (3):

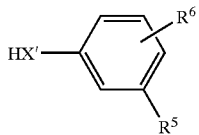

(3)

wherein $R^5$ and $R^6$; and $X'$ have the same meanings as defined above,
in a solvent in the presence of a base.

The third invention relates to a process for preparing the compound (1) represented by the above formula (1), which comprises allowing a compound (4) represented by the following formula (4):

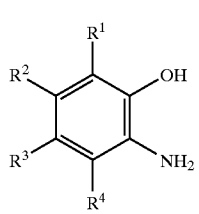

(4)

wherein $R^1$ to $R^4$ have the same meanings as defined above,
to react with a compound represented by the following formula (5):

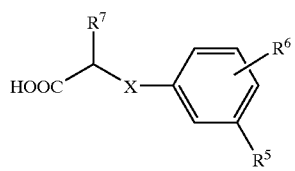

(5)

wherein $R^5$ to $R^7$ and X have the same meanings as defined above,
or a reactive derivative thereof.

The fourth invention relates to a compound represented by the following formula (6):

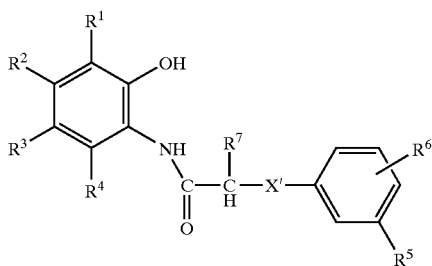

(6)

wherein $R^1$ to $R^7$ have the same meanings as defined above.

The fifth invention relates to a herbicide containing the above-mentioned compound (1) as an effective ingredient.

BEST MODE FOR CARRYING OUT THE INVENTION

In the following, the present invention is explained in detail.

Incidentally, in the explanation of the invention, it is mentioned as a compound (numeral) with an Arabic numeral with blankets attached to a chemical formula (for example, that shown by the formula (1) is also referred to as the compound (1).).

Symbols such as $R^1$ to $R^7$, X, X', Y, etc. shown in the compounds (1) to (6) of the present invention have the meanings as mentioned below. ($R^1$ to $R^4$)

As $R^1$ to $R^4$, there may be mentioned a hydrogen atom, an alkyl group having 1 to 6 carbon atoms, an alkoxy group having 1 to 4 carbon atoms, a haloalkoxy group having 1 to 4 carbon atoms, a halogen atom, a nitro group, a cyano group, a carboxyl group, an alkoxycarbonyl group having 2 to 5 carbon atoms, $R^8S(O)_n$ or $R^9NH$ group.

Incidentally, $R^8$ represents an alkyl group having 1 to 6 carbon atoms; n is an integer of 0 to 2; and $R^9$ represents a hydrogen atom, an alkyl group having 1 to 4 carbon atoms or an alkylcarbonyl group having 2 to 4 carbon atoms.

(1) In $R^1$ to $R^4$,
the alkyl group is a straight or branched one; preferably that having 1 to 4 carbon atoms; more preferably that having 1 to 3 carbon atoms (for example, there may be mentioned a methyl group, an ethyl group and a propyl group.).

The alkoxy group is a straight or branched one; preferably that having 1 to 4 carbon atoms; more preferably that having 1 to 3 carbon atoms (for example, there may be mentioned a methoxy group, an ethoxy group, a propyloxy group and an isopropyloxy group.).

The haloalkyl group is a straight or branched one; preferably that having 1 to 4 carbon atoms which has a fluorine atom, a chlorine atom, a bromine atom or an iodine atom; more preferably that having 1 to 3 carbon atoms (for example, there may be mentioned a chloromethyl group, a chloroethyl group and a trifluoromethyl group.).

The haloalkoxy group is a straight or branched one; preferably that having 1 to 4 carbon atoms; more preferably that having 1 to 3 carbon atoms which has a fluorine atom, a chlorine atom, a bromine atom or an iodine atom (for example, there may be mentioned a trifluoromethoxy group and a trifluoroethoxy group.).

The halogen atom is a fluorine atom, a chlorine atom, a bromine atom or an iodine atom; preferably a chlorine atom.

The alkoxycarbonyl group is a straight or branched one; preferably that having an alkoxy with 1 to 4 carbon atoms; more preferably that having an alkoxy with 1 to 3 carbon atoms (for example, there may be mentioned a methoxycarbonyl group, an ethoxycarbonyl group and an isopropoxycarbonyl group.).

(2) In $R^8$,
$R^6$ is a straight or branched alkyl group; preferably that having 1 to 4 carbon atoms; more preferably that having 1 to 3 carbon atoms (for example, there may be mentioned a methyl group.).

(3) In n,
n is an integer of 0, 1 or 2, preferably 0 or 2.

(4) In $R^9$,
as $R^9$, there may be mentioned a hydrogen atom, an alkyl group having 1 to 4 carbon atoms, an alkylcarbonyl group having 2 to 4 carbon atoms, or a trifluoromethylcarbonyl group.

The alkyl group is a straight or branched one; preferably those having 1 to 4 carbon atoms; more preferably those having 1 to 3 carbon atoms (for example, there may be mentioned a methyl group, an ethyl group, a propyl group.).

The alkylcarbonyl group is a straight or branched one; preferably those having alkyl with 1 to 3 carbon atoms; more preferably those having alkyl with 1 or 2 carbon atoms (for example, there may be mentioned a methylcarbonyl group, an ethylcarbonyl group.).
($R^5$)

As $R_5$, there may be mentioned a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group or $R^8S(O)_n$.

The alkyl group may be mentioned those described in the above-mentioned "(1) In $R^1$ to $R^4$".

The alkoxy group may be mentioned those described in the above-mentioned "(1) In $R^1$ to $R^4$".

The haloalkyl group may be mentioned those described in the above-mentioned "(1) In $R^1$ to $R^4$".

The haloalkoxy group may be mentioned those described in the above-mentioned "(1) In $R^1$ to $R^4$".

$R^8$ has the same meaning as defined above.

As $R^6$, there may be mentioned a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms.

The alkyl group may be mentioned those described in the above-mentioned "(1) In $R^1$ to $R^4$".

The alkoxy group may be mentioned those described in the above-mentioned "(1) In $R^1$ to $R^4$".
($R^7$)

As $R^7$, there may be mentioned a hydrogen atom, an alkyl group having 1 to 6 carbon atoms, a haloalkyl group having 1 to 4 carbon atoms or a phenyl group.

The alkyl group is a straight or branched one; preferably those having 1 to 4 carbon atoms; more preferably those having 1 to 3 carbon atoms (for example, there may be mentioned a methyl group, an ethyl group, a propyl group.).

The haloalkyl group is a straight or branched one; preferably those having a fluorine atom, a chlorine atom, a bromine atom or an iodine atom and having 1 to 4 carbon atoms; more preferably those having 1 to 3 carbon atoms (for example, there may be mentioned a chloromethyl group, a chloroethyl group and a trifluoromethyl group.).

As the phenyl group, an unsubstituted one or that having a substituent may be mentioned. (X)

As X, there may be mentioned O, S, SO or $SO_2$; preferably O. (X')

As X', there may be mentioned O or S; preferably O.

As the compound (1), those in which the above-mentioned various kinds of substituents are combined, and those preferred are as follows.

(1) A compound (1) wherein $R^1$, $R^3$ and $R^4$ are hydrogen atoms, $R^2$ and $R^6$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 9, 27, etc. mentioned in Table 1.

(2) A compound (1) wherein $R^1$, $R^3$, $R^4$ and $R^6$ are hydrogen atoms, $R^2$ is a halogen atom, $R^5$ is a haloalkyl group having 1 to 4 carbon atoms, $R^7$ is an alkyl group having 1 to 6 carbon atoms, and X is an oxygen atom.

For example, there may be mentioned Compound No. 10, etc. mentioned in Table 1.

(3) A compound (1) wherein $R^1$, $R^3$ and $R^4$ are hydrogen atoms, $R^2$ is a nitro group, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compound No. 39, etc. mentioned in Table 1.

(4) A compound (1) wherein $R^1$, $R^3$, $R^4$ and $R^6$ are hydrogen atoms, $R^2$ and $R^5$ are haloalkyl groups having 1 to 4 carbon atoms, $R^7$ is an alkyl group having 1 to 6 carbon atoms, and X is an oxygen atom.

For example, there may be mentioned Compounds Nos. 86, 94, etc. mentioned in Table 1.

(5) A compound (1) wherein $R^1$, $R^3$ and $R^4$ are hydrogen atoms, $R^2$ and $R^5$ are haloalkyl groups having 1 to 4 carbon atoms, $R^6$ is a halogen atom, $R^7$ is an alkyl group having 1 to 6 carbon atoms, and X is an oxygen atom.

For example, there may be mentioned.Compounds Nos. 93, 101, etc. mentioned in Table 1.

(6) A compound (1) wherein $R^1$, $R^2$ and $R^4$ are hydrogen atoms, $R^3$ and $R^6$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 119, 137, 139, 141, 165, 171, 438, 441, 476, etc. mentioned in Table 1.

(7) A compound (1) wherein $R^1$, $R^2$, $R^4$ and $R^6$ are hydrogen atoms, $R^3$ is a halogen atom, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 120, 138, 140, 142, 166, 172, etc. mentioned in Table 1.

(8) A compound (1) wherein $R^1$, $R^2$ and $R^4$ are hydrogen atoms, $R^3$ is a nitro group, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compounds Nos. 177, 432, etc. mentioned in Table 1.

(9) A compound (1) wherein $R^1$, $R^2$, $R^4$ and $R^6$ are hydrogen atoms, $R^3$ is a nitro group, $R^5$ is a haloalkyl group having 1 to 4 carbon atoms, $R^7$ is an alkyl group having 1 to 6 carbon atoms, and X is an oxygen atom.

For example, there may be mentioned Compound No. 178, etc. mentioned in Table 1.

(10) A compound (1) wherein $R^1$, $R^2$ and $R^4$ are hydrogen atoms, $R^3$ is a cyano group, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compound No. 189, etc. mentioned in Table 1.

(11) A compound (1) wherein $R^1$, $R^2$, $R^4$ and $R^6$ are hydrogen atoms, $R^3$ is a cyano group, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 190, 192, etc. mentioned in Table 1.

(12) A compound (1) wherein $R^1$, $R^2$ and $R^4$ are hydrogen atoms, $R^3$ and $R^5$ are haloalkyl groups having 1 to 4 carbon atoms, $R^6$ is a halogen atom, $R^7$ is an alkyl group having 1 to 6 carbon atoms, and x is an oxygen atom.

For example, there may be mentioned.Compounds Nos. 197, 199, etc. mentioned in Table 1.

(13) A compound (1) wherein $R^1$, $R^2$, $R^4$ and $R^6$ are hydrogen atoms, $R^3$ and $R^5$ are haloalkyl groups having 1 to 4 carbon atoms, $R^7$ is an alkyl group having 1 to 6 carbon atoms, and X is an oxygen atom.

For example, there may be mentioned Compounds Nos. 198, 200, etc. mentioned in Table 1.

(14) A compound (1) wherein $R^1$ and $R^4$ are hydrogen atoms, $R^2$, $R^3$ and $R^6$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 284, 286, 493, 494, etc. mentioned in Table 1.

(15) A compound (1) wherein $R^1$ and $R^4$ are hydrogen atoms, $R^2$ is a nitro group, $R^3$ and $R^6$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compound No. 334, etc. mentioned in Table 1.

(16) A compound (1) wherein $R^1$, $R^4$ and $R^6$ are hydrogen atoms, $R^2$ and $R^7$ are alkyl groups having 1 to 6 carbon atoms, $R^3$ is a halogen atom, $R^5$ is a haloalkyl group having 1 to 4 carbon atoms, and X is an oxygen atom.

For example, there may be mentioned Compound No. 339, etc. mentioned in Table 1.

(17) A compound (1) wherein $R^1$ and $R^4$ are hydrogen atoms, $R^2$ and $R^7$ are alkyl groups having 1 to 6 carbon atoms, $R^3$ and $R^6$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compound No. 340, etc. mentioned in Table 1.

(18) A compound (1) wherein $R^1$ and $R^4$ are hydrogen atoms, $R^2$ and $R^6$ are halogen atoms, $R^3$ is a cyano group, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 346, 348, 517, 530, 533, 534, etc. mentioned in Table 1.

(19) A compound (1) wherein $R^1$, $R^2$, $R^4$ and $R^6$ are hydrogen atoms, $R^3$ is a halogen atom, $R^5$ is a cyano group, $R^7$ is an alkyl group having 1 to 6 carbon atoms, and X is an oxygen atom.

For example, there may be mentioned Compounds Nos. 353, 457, etc. mentioned in Table 1.

(20) A compound (1) wherein $R^1$, $R^2$, $R^4$ and $R^6$ are hydrogen atoms, $R^3$ and $R^5$ are cyano groups, $R^7$ is an alkyl group having 1 to 6 carbon atoms, and X is an oxygen atom.

For example, there may be mentioned Compounds Nos. 392, 393, etc. mentioned in Table 1.

(21) A compound (1) wherein $R^1$, $R^2$, $R^4$ and $R^6$ are hydrogen atoms, $R^3$ is a cyano group, $R^5$ is a haloalkoxy group having 1 to 4 carbon atoms, $R^7$ is an alkyl group having 1 to 6 carbon atoms, and X is an oxygen atom.

For example, there may be mentioned Compound No. 396, etc. mentioned in Table 1.

(22) A compound (1) wherein $R^1$, $R^2$, $R^4$ and $R^6$ are hydrogen atoms, $R^3$ is a halogen atom, $R^5$ is a haloalkoxy group having 1 to 4 carbon atoms, $R^7$ is an alkyl group having 1 to 6 carbon atoms, and X is an oxygen atom.

For example, there may be mentioned Compound No. 447, etc. mentioned in Table 1.

(23) A compound (1) wherein $R^1$, $R^2$, $R^4$ and $R^6$ are hydrogen atoms, $R^3$ is a nitro group, $R^5$ is a haloalkoxy group having 1 to 4 carbon atoms, $R^1$ is an alkyl group having 1 to 6 carbon atoms, and X is an oxygen atom.

For example, there may be mentioned Compound No. 450, etc. mentioned in Table 1.

(24) A compound (1) wherein $R^1$ and $R^4$ are hydrogen atoms, $R^2$ is a cyano group, $R^3$ and $R^6$ are halogen atoms, $R^3$ is a cyano group, $R^5$ is a haloalkyl group having 1 to 4 carbon atoms, $R^7$ is an alkyl group having 1 to 6 carbon atoms, and X is an oxygen atom.

For example, there may be mentioned Compound No. 310, etc. mentioned in Table 1.

(25) A compound (1) wherein $R^1$, $R^4$ and $R^6$ are hydrogen atoms, $R^2$ and $R^3$ are cyano groups, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 315, 317, etc. mentioned in Table 1.

(26) A compound (1) wherein $R^1$ and $R^4$ are hydrogen atoms, $R^2$ and $R^3$ are cyano groups, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compounds Nos. 316, 318, etc. mentioned in Table 1.

(27) A compound (1) wherein $R^1$, $R^4$ and $R^6$ are hydrogen atoms, $R^2$ and $R^5$ are haloalkyl groups having 1 to 4 carbon atoms, $R^3$ is a halogen atom, $R^7$ is an alkyl group having 1 to 6 carbon atoms, and X is an oxygen atom.

For example, there may be mentioned Compounds Nos. 471, 474, etc. mentioned in Table 1.

(28) A compound (1) wherein $R^1$, $R^2$ and $R^4$ are hydrogen atoms, $R^3$ is an alkylsulfonyl group having 1 to 4 carbon atoms, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compounds Nos. 215, 217, etc. mentioned in Table 1.

(29) A compound (1) wherein $R^1$, $R^2$, $R^4$ and $R^6$ are hydrogen atoms, $R^3$ is an alkylsulfonyl group having 1 to 4 carbon atoms, $R^5$ is a haloalkyl group having 1 to 4 carbon atoms, $R^7$ is an alkyl group having 1 to 6 carbon atoms, and X is an oxygen atom.

For example, there may be mentioned Compound No. 216, etc. mentioned in Table 1.

(30) A compound (1) wherein $R^1$, $R^4$ and $R^6$ are hydrogen atoms, $R^2$ is an alkyl group having 1 to 6 carbon atoms, $R^3$ is a halogen atom, $R^5$ is a cyano group, $R^7$ is an alkyl group having 1 to 6 carbon atoms, and X is an oxygen atom.

For example, there may be mentioned Compounds Nos. 481, 484, etc. mentioned in Table 1.

(31) A compound (1) wherein $R^1$ and $R^4$ are hydrogen atoms, $R^2$ is an alkyl group having 1 to 6 carbon atoms, $R^3$ is an alkylsulfonyl group having 1 to 4 carbon atoms, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compounds Nos. 487, 488, etc. mentioned in Table 1.

(32) A compound (1) wherein $R^1$, $R^4$ and $R^6$ are hydrogen atoms, $R^2$ is an alkyl group having 1 to 6 carbon atoms, $R^5$ is an alkylsulfonyl group having 1 to 4 carbon atoms, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 489, 490, etc. mentioned in Table 1.

(33) A compound (1) wherein $R^1$, $R^4$ and $R^6$ are hydrogen atoms, $R^2$ is an alkyl group having 1 to 6 carbon atoms, $R^3$ is an alkylsulfonyl group having 1 to 4 carbon atoms, $R^5$ is a cyano group, $R^7$ is an alkyl group having 1 to 6 carbon atoms, and X is an oxygen atom.

For example, there may be mentioned Compounds Nos. 491, 492, etc. mentioned in Table 1.

(34) A compound (1) wherein $R^1$, $R^4$ and $R^6$ are hydrogen atoms, $R^2$ and $R^3$ are halogen atoms, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 496, 497, etc. mentioned in Table 1.

(35) A compound (1) wherein $R^1$, $R^4$ and $R^6$ are hydrogen atoms, $R^2$ and $R^3$ are halogen atoms, $R^5$ is a cyano group, $R^7$ is an alkyl group having 1 to 6 carbon atoms, and X is an oxygen atom.

For example, there may be mentioned Compounds Nos. 498, 501, etc. mentioned in Table 1.

(36) A compound (1) wherein $R^1$, $R^2$ and $R^4$ are hydrogen atoms, $R^3$ is an alkoxy group having 1 to 6 carbon atoms, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compound No. 503, etc. mentioned in Table 1.

(37) A compound (1) wherein $R^1$, $R^2$, $R^4$ and $R^6$ are hydrogen atoms, $R^3$ is an alkylsulfonyl group having 1 to 4 carbon atoms, $R^5$ is a cyano group, $R^7$ is an alkyl group having 1 to 6 carbon atoms, and X is an oxygen atom.

For example, there may be mentioned Compounds Nos. 507, 508, etc. mentioned in Table 1.

(38) A compound (1) wherein $R^1$, $R^2$ and $R^4$ are hydrogen atoms, $R^3$ is an alkylsulfonyl group having 1 to 4 carbon atoms, $R^5$ is a cyano group, $R^6$ is a halogen atom, $R^7$ is an alkyl group having 1 to 6 carbon atoms, and X is an oxygen atom.

For example, there may be mentioned Compound No. 509, etc. mentioned in Table 1.

(39) A compound (1) wherein $R^1$, $R^2$, $R^4$ and $R^6$ are hydrogen atoms, $R^3$ and $R^5$ are alkylsulfonyl groups having 1 to 4 carbon atoms, $R^7$ is an alkyl group having 1 to 6 carbon atoms, and X is an oxygen atom.

For example, there may be mentioned Compound No. 513, etc. mentioned in Table 1.

(40) A compound (1) wherein $R^1$, $R^2$ and $R^4$ are hydrogen atoms, $R^3$ is a trifluoromethylcarbonylamino group, $R^5$ is a haloalkyl group having 1 to 4 carbon atoms, $R^6$ is a halogen atom, $R^7$ is an alkyl group having 1 to 6 carbon atoms, and X is an oxygen atom.

For example, there may be mentioned Compound No. 518, etc. mentioned in Table 1.

(41) A compound (1) wherein $R^1$, $R^4$ and $R^6$ are hydrogen atoms, $R^2$ and $R^3$ are cyano groups, $R^5$ is a haloalkoxy group having 1 to 4 carbon atoms, $R^7$ is an alkyl group having 1 to 6 carbon atoms, and X is an oxygen atom.

For example, there may be mentioned Compound No. 527, etc. mentioned in Table 1.

(42) A compound (1) wherein $R^1$, $R^4$ and $R^6$ are hydrogen atoms, $R^2$ is a halogen atom, $R^3$ is a cyano group, $R^5$ is a haloalkyl group having 1 to 4 carbon atoms, $R^7$ is an alkyl group having 1 to 6 carbon atoms, and X is an oxygen atom.

For example, there may be mentioned Compounds Nos. 529, 532, etc. mentioned in Table 1.

The compound (1) of the present invention wherein X is an oxygen atom or a sulfur atom (Compound (1')) can be obtained by allowing Compound (2) to react with Compound (3) in a solvent in the presence of a base as mentioned below.

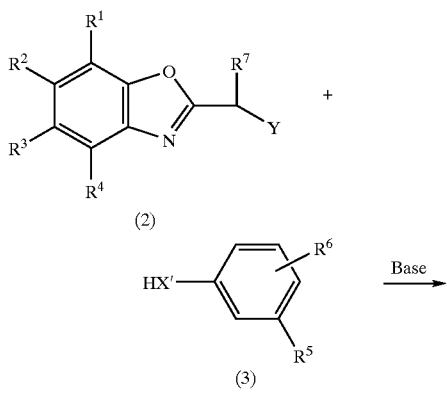

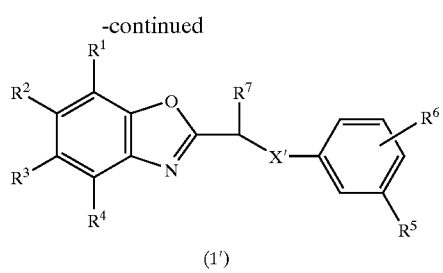

wherein $R^1$ to $R^7$, X' and Y have the same meanings as defined above.

The compound (2) can be easily produced by reacting a 2-aminophenol compound which is produced by the method as disclosed in, for example, Japanese Provisional Patent Publication No 45735/1998, Heterocycle, vol. 41, pp. 477–485 (1995), Synthetic Communication, vol. 19, pp. 2921–2924 (1989), Journal of Medicinal Chemistry, vol. 30, pp. 400–405 (1987), etc., with a 2-halocarboxylic acid.

As the compound (3), for example, a phenol compound or a thiphenol compound commercially available or those synthesized by the conventional manner can be employed for the reaction.

Or else, the compound (1) can be produced by reacting a compound (4) and a compound (5) or a reactive derivative thereof in a solvent, and, if necessary, by using a base or an acid catalyst as shown below.

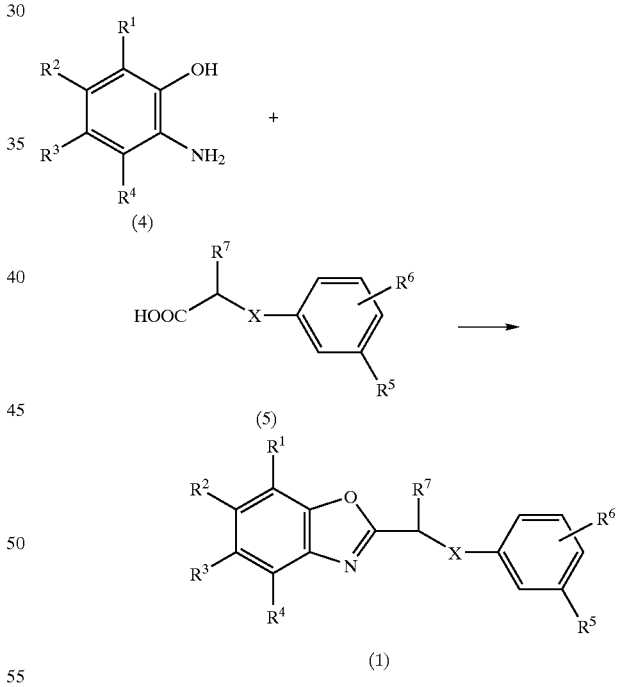

wherein, $R^1$ to $R^7$ and X have the same meanings as defined above.

The compound (4) can be obtained, for example, by reducing a nitrophenol compound which is commercially available or synthesized by the conventional manner.

The compound (5) can be easily produced by reacting a 2-haloalkane compound with a phenol compound or a thiophenol compound by the conventional manner.

And by reacting the compound (4) and the compound (5), before forming the compound (1), a compound (6) which is represented by the following formula (6):

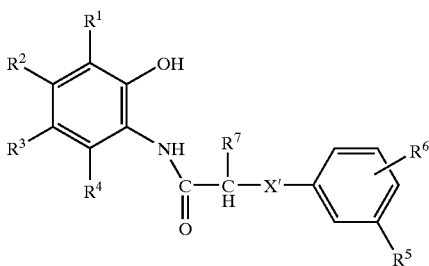

(6)

wherein, $R^2$ to $R^7$ and X have the same meanings as defined above, and is an intermediate is formed.

Thus, as a synthetic method of the compound (1), the compound (1) is produced by using the compound (6) once isolated, or the compound (1) can be produced by reacting the same without isolation.

Specific examples of the compound (1) may be mentioned those of Compounds 1 to 536shown in Table 1, and the like.

Specific examples of the compound (6) may be mentioned those of Compounds (6-1) to,(6-4) shown in Table 2, and the like.

As the solvent to be used in synthesis of the compound (1), it is not specifically limited so long as it is not participate in the present reaction directly, and may mentioned, for example, an ether such as diethyl ether, tetrahydrofuran, dioxane, etc.; a dipolar aprotic solvent such as N,N-dimethylformamide, dimethylsulfoxide, etc.; an aromatic hydrocarbon such as benzene, toluene, xylene, etc.; a nitrile such as acetonitrile, etc.; a ketone such as acetone, methyl ethyl ketone, etc.; an organic acid such as formic acid, acetic acid, propionic acid, etc., and a mixed solvent of the above solvents, and the like.

As a kind of the base to be used for production of the compound (1), there may be mentioned, for example, an organic base such as triethylamine, pyridine, 4-N,N-dimethylaminopyridine, N,N-dimethylaniline, 1,4-diazabicyclo [2.2.2]octane, 1,8-diazabicyclo[5.4.0]undeca-7-ene, etc.; alkali metal alkoxide such as sodium methoxide, sodium ethoxide, potassium-t-butoxide, etc.; an inorganic base such as sodium hydride, potassium hydride, sodium amide, sodium hydroxide, potassium hydroxide, potassium carbonate, sodium carbonate, potassium hydrogen carbonate, sodium hydrogen carbonate, etc.; lithium diisopropylamide, bistrimethylsilyl lithium amide.

As a kind of the acid catalyst, there may be mentioned, for example, a mineral acid such as hydrochloric acid, sulfuric acid, nitric acid, etc.; an organic acid such as formic acid, acetic acid, propionic acid, methanesulfonic acid, benzenesulfonic acid, p-toluenesulfonic acid monohydrate, etc.; an acid addition salt of an amine such as pyridine hydrochloride, triethyleamine hydrochloride, etc.; a metal halide such as titanium tetrachloride, zinc chloride, ferrous chloride, ferric chloride, etc.; a Lewis acid such as boron trifluoride-etherate, etc.

An amount of the base catalyst or the acid catalyst to be used is 0.001 to 1-fold mole based on that of the compound (2).

The production method of the compound (1) can be carried out with a reaction concentration of 5 to 80%.

In the production method, the base can be added with a ratio of 0.5 to 2 moles per mole of the compound (2), preferably 1 to 1.2 moles.

The reaction temperature is not specifically limited so long as it is carried out at a boiling point or lower of the solvent to be used, and it is usually carried out at 0 to 110° C.

The reaction time may vary depending on the above-mentioned concentration and temperature, and usually carried out for 0.5 to 24 hours.

The herbicide of the present invention has a remarkable herbicidal effect by bleaching effect, and contains one or more kinds of the compound (1) as an effective ingredient.

The active compound of the present invention is effective for monocotyledonus weeds and dicotyledonus weeds, and can be used as a herbicide for paddy fields and upland fields.

As the monocotyledonus weeds, there may be mentioned paddy field weeds such as barnyardgrass (*Echinochloa crusgalli*), bulrush (*Scrips juncoides*), flat sedge (*Cyperus serotinus*), smallflower umbrellaplant (*Cyperus difformis*), narrowleaf water plantain (*Alisma canaliculatum*), Monochoria (*Monochoria vaginalis*), arrowhead (*Sagittaria pygmaea*), etc.; and upland field weeds such as crabgrass (*Digitaria adscendens*), goosegrass (*Eleusine indica*), green foxtail (*Setaria viridis*), blackgrass (*Alopecurus aegualis*), annual bluegrass (*Poa annua*), etc.

As the dicotyledonus weeds, there may be mentioned paddy field weeds such as False pimpernel (*Lindernia pyxidaria*), Toothcup (*Rotala indica*), Dropwort (*Oenanthe javanica*), etc.; and upland field weeds such as common lambsquarters (*Chenopodium album*), livid amaranth (*Amaranthus lividus*), velvetcaf (*Abutilon theophrasti*), morning glory (Ipomoea spps.), common cocklebur (*Xanthium pensylvanicum*), Cassia obtusifolia, Chickweed (*Stellaria media*), etc.

The active compound of the present invention can be applied either before germination or after germination of plants, and may be mixed with soil before seeding An amount of the active compound of the present invention to be applied can be changed with a wide range depending on a kind of the compound, a kind of plants to be applied, a time to be applied, a place to be applied, qualities of effects to be desired, and the like, and as a general standard, it can be exemplified by a range of about 0.001 to 10 kg, preferably about 0.01 to 1 kg per hectare (ha) of the active compound The compound (1) can be used alone, but usually used by formulating a diluent, a surfactant, a dispersant, an auxiliary, etc., according to the conventional manner, and for example, it is preferably prepared as a composition such as a dust, an emulsion, fine granule, granule, wettable powder, granular wettable powder, an aqueous suspension, an oily suspension, an emulsified dispersion, a soluble preparation, an oily agent, a microcapsule, etc.

As a solid diluent, there may be mentioned, for example, talc, bentonite, montmorillonite, clay, kaolin, calcium carbonate, diatomaceous earth, white carbon, vermiculite, slaked lime, siliceous sand, ammonium sulfate, urea, etc. As a liquid diluent, there may be mentioned, for example, hydrocarbons such as kerosene, mineral oil, etc.; aromatic hydrocarbons such as benzene, toluene, xylene, dimethylnaphthalene, phenylxylylethane, etc.; chlorinated hydrocarbons such as chloroform, carbon tetrachloride, etc.; ethers such as dioxane, tetrahydrofuran, etc.; ketones such as acetone, cyclohexanone, isophorone, etc.; esters such as ethyl acetate, ethylene glycol acetate, dibutyl maleate, etc.; alcohols such as methanol, n-hexanol, ethylene glycol, etc.; polar solvents such as dimethylformamide, dimethylsulfoxide, N-methylpyrrolidone, etc.; water and the like.

As a sticking agent and a dispersant, there may be mentioned, for example, casein, polyvinyl alcohol, carboxymethyl cellulose, bentonite, xanthene gum, gum arabic, etc.

As an aerosol propellant, there may be mentioned, for example, air, nitrogen, carbon dioxide gas, propane, halogenated hydrocarbons, etc.

As a surfactant, there may be mentioned, for example, an alkylsulfate, an alkylsulfonate, an alkylbenzenesulfonate, a ligninesulfonate, a dialkylsulfosuccinate, a naphthalenesulfonate condensate, a polyoxyethylene alkyl ether, a polyoxyethylene alkyl allyl ether, a polyoxyethylene alkyl ester, an alkyl sorbitan ester, a polyoxyethylene sorbitan ester, a polyoxyethylene alkylamine, etc.

In the preparation of the present preparation, the above-mentioned diluent, surfactant, dispersant and auxiliary may be used each singly or in a suitable combination of two or more depending on the respective purposes.

A concentration of an effective ingredient when the compound (1) of the present invention is made into preparations is generally 1 to 50% by weight in an emulsion, generally 0.3 to 25% by weight in a dust, generally 1 to 90% by weight in a wettable powder or a granular wettable powder, generally 0.5 to 10% by weight in a granule, generally 0.5 to 40% by weight in a dispersion, generally 1 to 30% by weight in an emulsified dispersion, generally 0.5 to 20% by weight in a soluble preparation, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLES

In the following, the present invention is specifically explained by referring to Examples. Incidentally, these Examples is not limit the scope of the present invention.

EXAMPLE 1

Synthesis of the Compound (1)
(1) Synthesis of 1-(5-fluorobenzoxazol-2-yl)-1-(4-fluoro-3-(trifluoromethyl)phenoxy)propane (Compound 119)
First step:
Into 30 g of 2-(4-fluoro-3-(trifluoro-methyl)phenoxy) butanoic acid was added dropwise 15 m of thionyl chloride under ice-cooling.

After completion of the dropwise addition, the mixture was refluxed for 2 hours, and thionyl chloride was removed under reduced pressure to give 32.8 g of 2-(4-fluoro-3-(trifluoromethyl)phenoxy)butanoic chloride.

Second step:
In 50 ml of acetic acid was dissolved 0.50 g (3.94 mmol) of 2-amino-4-fluorophenol, and 1.12 g (3.94 mmol) of 2-(4-fluoro-3-(trifluoromethyl)phenoxy)butanoic chloride was added to the above solution and the mixture was stirred at 50 to 60° C. for one hour.

The residue obtained by removing acetic acid by distillation under reduced pressure was dissolved in 30 ml of toluene-acetic acid (1:1), and a few drops of sulfuric acid was added to the solution and the mixture was refluxed for 6 hours.

After cooling to room temperature, ethyl acetate was added to the reaction mixture and the organic layer was washed successively with water and a saturated saline solution, and dried over anhydrous sodium sulfate.

The resulting residue was isolated by column chromatography (Wakogel C-300 available from Wako Junyaku Co., eluted by n-hexane;ethyl acetate=9:1) to obtain 0.38 g (yield was 27%) of the title compound which is a title compound as an oily product.

(2) Synthesis of 1-(5-chlorobenzoxazol-2-yl)-1-(3-(trifluoromethyl)phenoxy)butane (Compound 142)

In 20 ml of acetonitrile were dissolved 0.19 g (1.16 mmol) of 3-trifluoromethylphenol, 0.28 g (0.97 mmol) of 1-(5-chlorobenzoxazol-2-yl)butyl bromide and 0.2 g (1.46 mmol) of potassium carbonate, and the solution was refluxed for one hour.

After cooling to room temperature, acetonitrile was removed by distillation under reduced pressure and the residue was dissolved in toluene.

The toluene layer was washed with water and 2N sodium hydroxide, dried over anhydrous sodium sulfate and toluene was removed by distillation under reduced pressure, and the obtained residue was isolated by column chromatography (Wakogel C-300 available from Wako Junyaku Co., eluted by n-hexane:ethyl acetate=15:1) to obtain 0.36 g (yield was 100%) of the title compound as an oily product.

(3) Synthesis of 1-(5-nitrobenzoxazol-2-yl)-1-(3-(trifluoromethyl)phenoxy)ethane (Compound 176)
First step:
8 ml of thionyl chloride was added dropwise under ice-cooling to 10 g of 2-(3-(trifluoro methyl)phenoxy) propionic acid.

After completion of the dropwise addition, the mixture was refluxed for 2 hours, and thionyl chloride was removed by distillation under reduced pressure to obtain 9.8 g of 2-(3-(trifluoromethyl)phenoxy)propionic chloride.

Second step: In 50 ml of xylene were dissolved 0.66 g (2.60 mmol) of 2-(3-(trifluoromethyl)phenoxy)propionic chloride, 0.40 g (2.60 mmol) of 2-amino-4-nitrophenol and 0.1 g of p-toluenesulfonic acid monoacid hydrate, and the solution was refluxed for 4 hours.

After cooling to room temperature, xylene was removed by distillation under reduced pressure and the resulting residue was isolated by column chromatography (Wakogel C-300 available from Wako Junyaku Co., eluted by n-hexane:ethyl acetate=15:1) to obtain 0.57 g (yield was 62%) of the title compound as an oily product. (4) Synthesis of 1-(5-chloro-6-methylbenzoxazol-2-yl)-1-(3-(trifluoromethyl)phenoxy)propane (Compound 339)

In 50 ml of xylene were dissolved 0.53 g (1.99 mmol) of 2-(3-(trifluoromethyl)phenoxy)butanoic chloride, 0.31 g (1.99 mmol) of 2-amino-4-chloro-5-methylphenol and 0.05 g of p-toluenesulfonic acid monoacid hydrate, and the solution was refluxed for 8 hours.

After cooling to room temperature, the reaction mixture was washed with 2N sodium hydroxide, the organic layer was dried over anhydrous sodium sulfate, and xylene was removed by distillation under reduced pressure to obtain 0.35 g (yield was 48%) of the title compound as an oily product.

(5) Synthesis of 1-(5-cyanobenoxazol-2-yl)-1-(3,4-dicyanophenoxy)-2-methylpropane (Compound 401)

In 20 ml of acetonitrile were dissolved 0.15 g (1.07 mmol) of 4-hydroxyphthalonitrile, 0.25 g (0.90 mmol) of 1-(5-cyanobenzoxazol-2-yl)-2-methylpropyl bromide and 0.2 g (1.46 mmol) of potassium carbonate, and the solution was refluxed for 2 hours.

After cooling to room temperature, acetonitrile was removed by distillation under reduced pressure and the residue was dissolved again in toluene.

The toluene layer was washed with water and 2N sodium hydroxide, dried over anhydrous sodium sulfate, and the residue obtained by removing toluene by distillation under reduced pressure was isolated by column chromatography (Wakogel C-300 available from Wako Junyaku Co., eluted by n-hexane:ethyl acetate=2:1) to obtain 0.06 g (yield was 19%) of the title compound as an oily product.

(6) Synthesis of 1-(5-(trifluoromethyl)benzoxazol-2-yl)-1-(3-(trifluoromethyl)phenylthio)propane (Compound 258)

First step:

5 ml of thionyl chloride was added dropwise to 3 g of 2-(3-(trifluoromethyl)phenylthio)-butanoic acid under ice-cooling.

After completion of dropwise addition, thionyl chloride was removed by distillation under reduced pressure to obtain 2.9 g of 2-(3-(trifluoromethyl)phenylthio)-butanoic acid chloride.

Second step:

In 20 ml of xylene were dissolved 0.61 g (2.16 mmol) of 2-(3-(trifluoromethyl)phenylthio)butanoic acid chloride, 0.38 g (2.16 mmol) of 2-amino-4-trifluoro-methylphenol and 0.15 g of p-toluenesulfonic acid monohydrate, and the solution was refluxed for 4 hours.

After cooling to room temperature, the residue obtained by removing xylene by distillation under reduced pressure was isolated by column chromatography (Wakogel C-300 available from Wako Junyaku Co., eluted by n-hexane: ethyl acetate=15:1) to obtain 0.53 g (yield was 61%) of the title compound as an oily product.

(7) Synthesis of 1-(5-(trifluoromethyl)benzoxazol-2-yl)-1-(3-(trifluoromethyl)phenylsulfonyl)propane (Compound 270)

In methylene chloride was dissolved 0.28 g (0.69 mmol) of 1-(5-(trifluoromethyl)benzoxazol-2-yl)-1-(3-(trifluoromethyl)phenylthio)propane, and under ice-cooling, 0.26 g (1.04 mmol) of m-chloroperbenzoic acid (purity: 70%) was added to the solution.

After stirring at room temperature for one hour, an aqueous sodium thiosulfate solution was added to the mixture and the resulting mixture was stirred for 15 minutes.

After separating the organic layer, it was washed with a saturated sodium bicarbonate solution, dried over anhydrous sodium sulfate and the solvent was removed by distillation.

The resulting residue was isolated by column chromatography (Wakogel C-300 available from Wako Junyaku Co., eluted by n-hexane:ethyl acetate=2:1) to obtain 0.13 g (yield was 43%) of the title compound as an oily product.

(8) Synthesis of 1-(5-chloro-6-fluorobenzoxazol-2-yl)-1-(4-fluoro-3-(trifluoromethyl)phenoxy)butane (Compound 294)

First step:

8 ml of thionyl chloride was added dropwise to 10 g of 2-(4-fluoro-3-(trifluoromethyl)phenoxy)valeric acid under ice-cooling After completion of dropwise addition, thionyl chloride was removed by distillation under reduced pressure to obtain 10.7 g of 2-(4-fluoro-3-(trifluoromethyl)phenoxy)valeric acid chloride.

Second step:

In 20 ml of xylene were dissolved 0.15 g (0.93 mmol) of 2-(4-fluoro-3-(trifluoromethyl)phenyoxy)valeric acid chloride, 0.05 g of p-toluenesulfonic acid monohydrate and 1.12 g (3.94 mmol) of 2-(4-fluoro-3-(trifluoromethyl)phenoxy)butanoic acid chloride, and the solution was refluxed for 5 hours.

After cooling to room temperature, the residue obtained by removing xylene by distillation under reduced pressure was isolated by column chromatography (Wakogel C-300 available from Wako Junyaku Co., eluted by n-hexane:ethyl acetate=15:1) to obtain 0.23 g (yield was 61%) of the title compound as an oily product.

(9) Synthesis of 1-(5-chloro-6-nitrobenzoxazol-2-yl)-1-(4-fluoro-3-(trifluoromethyl)phenoxy)propane (Compound 334)

First step:

In 30 ml of acetic acid was dissolved 0.91 g (4.83 mmol) of 2-amino-4-chloro-5-nitrophenol, and 1.37 g (4.83 mmol) of 2-(4-fluoro-3-(trifluoromethyl)phenoxy)butanoic acid chloride and the mixture was refluxed for 3 hours.

After cooling to room temperature, water was added to the reaction mixture and the mixture was extracted by ethyl acetate.

The organic layer was dried over anhydrous sodium sulfate, and the residue obtained by removing ethyl acetate by distillation under reduced pressure was suspended by hexane and the mixture was filtered to obtain 1.57 g (yield was 74%) of N-(5-chloro-2-hydroxy-4-nitrophenyl)-2-(4-fluoro-3-(trifluoromethyl)phenoxy)butanoic amide (Compound (6-3)) as pale brownish powder (melting point 181–183° C).

Second step:

In 50 ml of toluene was dissolved 1.37 g (3.14 mmol) of the obtained amide compound (Compound (6-3)), and four drops of conc. sulfuric acid were added to the solution, and the mixture was refluxed for 3 hours.

After cooling to room temperature, the toluene layer was washed with water and a saturated saline solution, dried over anhydrous sodium sulfate, and toluene was removed under reduced pressure. The resulting residue was isolated by column chromatography (Wakogel C-300 available from Wako Junyaku Co., eluted by n-hexane:ethyl acetate=8:1) to obtain 0.66 g (yield was 50%) of the title compound as an oily product. (10) Syntheses of Compound (1) and Compound (6) in Table 1 and Table 2

In accordance with the methods as mentioned in the above (1) to (9), the other compounds (1) and the compounds (6) shown in Table 1 and Table 2 were synthesized.

The compound (1), the compound (6) and their physical properties of the compound synthesized as mentioned in Table 1 to Table 3 were shown.

TABLE 1

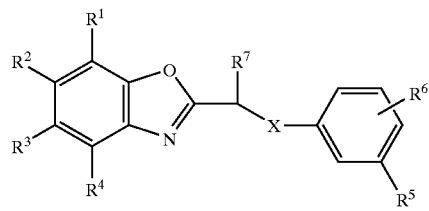

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 1 | Cl | H | H | H | $CF_3$ | H | $C_2H_5$ | O | |
| 2 | Cl | H | H | H | $CF_3$ | 4-F | $C_2H_5$ | O | |
| 3 | H | Cl | H | H | $CF_3$ | H | $CH_3$ | S | |
| 4 | H | Cl | H | H | $CF_3$ | 4-F | $CH_3$ | S | |
| 5 | Cl | Cl | H | H | $CF_3$ | H | $C_2H_5$ | S | |
| 6 | Cl | Cl | H | H | $CF_3$ | 4-F | $C_2H_5$ | S | |
| 7 | H | Cl | H | H | $CF_3$ | H | $CH_3$ | O | |
| 8 | H | Cl | H | H | $CF_3$ | 4-F | $CH_3$ | O | |
| 9 | H | Cl | H | H | $CF_3$ | 4-F | $C_2H_5$ | O | See Table 3 |
| 10 | H | Cl | H | H | $CF_3$ | H | $C_2H_5$ | O | See Table 3 |
| 11 | H | Cl | H | H | $CF_3$ | 4-F | $C_3H_7$-n | O | |
| 12 | H | Cl | H | H | $CF_3$ | H | $C_3H_7$-n | O | |
| 13 | H | Cl | H | H | $CF_3$ | 4-F | $C_3H_7$-i | O | |
| 14 | H | Cl | H | H | $CF_3$ | H | $C_3H_7$-i | O | |
| 15 | H | Cl | H | H | $CF_3$ | 4-F | $C_4H_9$-n | O | |
| 16 | H | Cl | H | H | $CF_3$ | H | $C_4H_9$-n | O | |
| 17 | H | Cl | H | H | $CF_3$ | 4-F | $C_4H_9$-i | O | |
| 18 | H | Cl | H | H | $CF_3$ | H | $C_4H_9$-i | O | |
| 19 | H | Cl | H | H | $CF_3$ | 4-F | $C_4H_9$-i | O | |
| 20 | H | Cl | H | H | $CF_3$ | H | $C_4H_9$-i | O | |
| 21 | H | Cl | H | H | $CF_3$ | 4-F | $C_4H_9$-s | O | |
| 22 | H | Cl | H | H | $CF_3$ | H | $C_4H_9$-s | O | |
| 23 | H | Cl | H | H | $CF_3$ | 4-F | $C_4H_9$-t | O | |
| 24 | H | Cl | H | H | $CF_3$ | H | $C_4H_9$-t | O | |
| 25 | H | F | H | H | $CF_3$ | 4-F | $CH_3$ | O | |
| 26 | H | F | H | H | $CF_3$ | H | $CH_3$ | O | |
| 27 | H | F | H | H | $CF_3$ | 4-F | $C_2H_5$ | O | See Table 3 |
| 28 | H | F | H | H | $CF_3$ | H | $C_2H_5$ | O | |
| 29 | H | F | H | H | $CF_3$ | 4-F | $C_3H_7$-n | O | |
| 30 | H | F | H | H | $CF_3$ | H | $C_3H_7$-n | O | |
| 31 | H | Br | H | H | $CF_3$ | 4-F | $CH_3$ | O | |
| 32 | H | Br | H | H | $CF_3$ | H | $CH_3$ | O | |
| 33 | H | Br | H | H | $CF_3$ | 4-F | $C_2H_5$ | O | |
| 34 | H | Br | H | H | $CF_3$ | H | $C_2H_5$ | O | |
| 35 | H | Br | H | H | $CF_3$ | 4-F | $C_3H_7$-n | O | |
| 36 | H | Br | H | H | $CF_3$ | H | $C_3H_7$-n | O | |
| 37 | H | $NO_2$ | H | H | $CF_3$ | 4-F | $CH_3$ | O | |
| 38 | H | $NO_2$ | H | H | $CF_3$ | H | $CH_3$ | O | |
| 39 | H | $NO_2$ | H | H | $CF_3$ | 4-F | $C_2H_5$ | O | See Table 3 |
| 40 | H | $NO_2$ | H | H | $CF_3$ | H | $C_2H_5$ | O | |
| 41 | H | $NO_2$ | H | H | $CF_3$ | 4-F | $C_3H_7$-n | O | |
| 42 | H | $NO_2$ | H | H | $CF_3$ | H | $C_3H_7$-n | O | |
| 43 | H | CN | H | H | $CF_3$ | 4-F | $CH_3$ | O | |
| 44 | H | CN | H | H | $CF_3$ | H | $CH_3$ | O | |
| 45 | H | CN | H | H | $CF_3$ | 4-F | $C_2H_5$ | O | |
| 46 | H | CN | H | H | $CF_3$ | H | $C_2H_5$ | O | |
| 47 | H | CN | H | H | $CF_3$ | 4-F | $C_3H_7$-n | O | |
| 48 | H | CN | H | H | $CF_3$ | H | $C_3H_7$-n | O | |
| 49 | H | H | H | $CH_3$ | $CF_3$ | 4-F | $CH_3$ | O | |
| 50 | H | H | H | $CH_3$ | $CF_3$ | H | $CH_3$ | O | |
| 51 | H | H | H | $CH_3$ | $CF_3$ | 4-F | $C_2H_5$ | O | See Table 3 |
| 52 | H | H | H | $CH_3$ | $CF_3$ | H | $C_2H_5$ | O | |
| 53 | H | H | H | $CH_3$ | $CF_3$ | 4-F | $C_3H_7$-n | O | |
| 54 | H | H | H | $CH_3$ | $CF_3$ | H | $C_3H_7$-n | O | |
| 55 | $NO_2$ | H | H | H | $CF_3$ | 4-F | $CH_3$ | O | |
| 56 | $NO_2$ | H | H | H | $CF_3$ | H | $CH_3$ | O | |
| 57 | $NO_2$ | H | H | H | $CF_3$ | 4-F | $C_2H_5$ | O | See Table 3 |

TABLE 1-continued

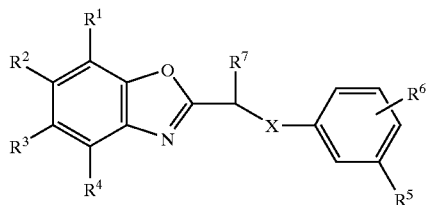

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 58 | $NO_2$ | H | H | H | $CF_3$ | H | $C_2H_5$ | O | |
| 59 | $NO_2$ | H | H | H | $CF_3$ | 4-F | $C_3H_7$-n | O | |
| 60 | $NO_2$ | H | H | H | $CF_3$ | H | $C_3H_7$-n | O | |
| 61 | $NH_2$ | H | H | H | $CF_3$ | 4-F | $CH_3$ | O | |
| 62 | $NH_2$ | H | H | H | $CF_3$ | H | $CH_3$ | O | |
| 63 | $NH_2$ | H | H | H | $CF_3$ | 4-F | $C_2H_5$ | O | See Table 3 |
| 64 | $NH_2$ | H | H | H | $CF_3$ | H | $C_2H_5$ | O | |
| 65 | $NH_2$ | H | H | H | $CF_3$ | 4-F | $C_3H_7$-n | O | |
| 66 | $NH_2$ | H | H | H | $CF_3$ | H | $C_3H_7$-n | O | |
| 67 | $CH_3CONH$ | H | H | H | $CF_3$ | 4-F | $CH_3$ | O | |
| 68 | $CH_3CONH$ | H | H | H | $CF_3$ | H | $CH_3$ | O | |
| 69 | $CH_3CONH$ | H | H | H | $CF_3$ | 4-F | $C_2H_5$ | O | See Table 3 |
| 70 | $CH_3CONH$ | H | H | H | $CF_3$ | H | $C_2H_5$ | O | |
| 71 | $CH_3CONH$ | H | H | H | $CF_3$ | 4-F | $C_3H_7$-n | O | |
| 72 | $CH_3CONH$ | H | H | H | $CF_3$ | H | $C_3H_7$-n | C | |
| 73 | Cl | H | $CF_3$ | H | $CF_3$ | 4-F | $CH_3$ | O | |
| 74 | Cl | H | $CF_3$ | H | $CF_3$ | H | $CH_3$ | O | |
| 75 | Cl | H | $CF_3$ | H | $CF_3$ | 4-F | $C_2H_5$ | O | See Table 3 |
| 76 | Cl | H | $CF_3$ | H | $CF_3$ | H | $C_2H_5$ | O | See Table 3 |
| 77 | Cl | H | $CF_3$ | H | $CF_3$ | 4-F | $C_3H_7$-n | O | |
| 78 | Cl | H | $CF_3$ | H | $CF_3$ | H | $C_3H_7$-n | O | |
| 79 | Cl | H | H | H | $CF_3$ | 4-F | $CH_3$ | O | |
| 80 | Cl | H | H | H | $CF_3$ | H | $CH_3$ | O | |
| 81 | Cl | H | H | H | $CF_3$ | 4-F | $C_2H_5$ | O | See Table 3 |
| 82 | Cl | H | H | H | $CF_3$ | H | $C_2H_5$ | O | |
| 83 | Cl | H | H | H | $CF_3$ | 4-F | $C_3H_7$-n | O | |
| 84 | Cl | H | H | H | $CF_3$ | H | $C_3H_7$-n | O | |
| 85 | H | $CF_3$ | H | H | $CF_3$ | 4-F | $CH_3$ | O | |
| 86 | H | $CF_3$ | H | H | $CF_3$ | H | $CH_3$ | O | See Table 3 |
| 87 | H | $CF_3$ | F | H | $CF_3$ | 4-F | $C_2H_5$ | O | |
| 88 | H | $CF_3$ | F | H | $CF_3$ | H | $C_2H_5$ | O | |
| 89 | H | $CF_3$ | F | H | $CF_3$ | 4-F | $C_3H_7$-n | O | |
| 90 | H | $CF_3$ | F | H | $CF_3$ | H | $C_3H_7$-n | O | |
| 91 | H | $CF_3$ | F | H | $CF_3$ | 4-F | $CH_3$ | O | |
| 92 | H | $CF_3$ | F | H | $CF_3$ | H | $CH_3$ | O | |
| 93 | H | $CF_3$ | H | H | $CF_3$ | 4-F | $C_2H_5$ | O | See Table 3 |
| 94 | H | $CF_3$ | H | H | $CF_3$ | H | $C_2H_5$ | O | See Table 3 |
| 95 | H | $CF_3$ | Cl | H | $CF_3$ | H | $C_3H_7$-n | O | |
| 96 | H | $CF_3$ | Cl | H | $CF_3$ | H | $C_3H_7$-n | O | |
| 97 | H | $CF_3$ | Cl | H | $CF_3$ | 4-F | $CH_3$ | O | |
| 98 | H | $CF_3$ | Cl | H | $CF_3$ | H | $CH_3$ | O | |
| 99 | H | $CF_3$ | Cl | H | $CF_3$ | 4-F | $C_2H_5$ | O | |
| 100 | H | $CF_3$ | Cl | H | $CF_3$ | H | $C_2H_5$ | O | |
| 101 | H | $CF_3$ | H | H | $CF_3$ | 4-F | $C_3H_7$-n | O | See Table 3 |
| 102 | H | $CF_3$ | H | H | $CF_3$ | H | $C_3H_7$-n | O | |
| 103 | H | CN | H | H | $CF_3$ | H | $CH_3$ | O | |
| 104 | H | CN | H | H | $CF_3$ | H | $CH_3$ | O | |
| 105 | H | CN | H | H | $CF_3$ | H | $C_2H_5$ | O | |
| 106 | H | CN | H | H | $CF_3$ | H | $C_2H_5$ | O | |
| 107 | H | CN | H | H | $CF_3$ | H | $C_3H_7$-n | O | |
| 108 | H | CN | H | H | $CF_3$ | H | $C_3H_7$-n | O | |
| 109 | H | H | F | Cl | $CF_3$ | 4-F | $C_2H_5$ | O | |
| 110 | H | H | F | Cl | $CF_3$ | H | $C_2H_5$ | O | |
| 111 | H | H | F | H | $CF_3$ | 4-F | $CH_3$ | S | |

TABLE 1-continued

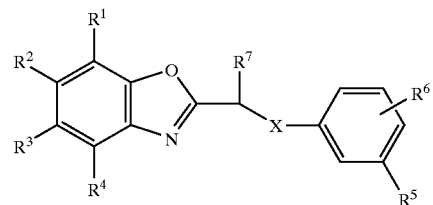

(1)

| Compound | R¹ | R² | R³ | R⁴ | R⁵ | R⁶ | R⁷ | X | Physical property |
|---|---|---|---|---|---|---|---|---|---|
| 112 | H | H | F | H | $CF_3$ | H | $CH_3$ | S | |
| 113 | H | H | F | Cl | $CF_3$ | 4-F | $CH_3$ | O | |
| 114 | H | H | F | Cl | $CF_3$ | H | $CH_3$ | O | |
| 115 | Cl | H | F | H | $CF_3$ | 4-F | $C_2H_5$ | S | |
| 116 | Cl | H | F | H | $CF_3$ | H | $C_2H_5$ | S | |
| 117 | H | H | F | H | $CF_3$ | 4-F | $CH_3$ | O | |
| 118 | H | H | F | H | $CF_3$ | H | $CH_3$ | O | |
| 119 | H | H | F | H | $CF_3$ | 4-F | $C_2H_5$ | O | See Table 3 |
| 120 | H | H | F | H | $CF_3$ | H | $C_2H_5$ | O | See Table 3 |
| 121 | H | H | F | H | $CF_3$ | 4-F | $C_3H_7$-n | O | |
| 122 | H | H | F | H | $CF_3$ | H | $C_3H_5$-n | O | |
| 123 | H | H | F | H | $CF_3$ | 4-F | $C_3H_7$-i | O | |
| 124 | H | H | F | H | $CF_3$ | H | $C_3H_7$-i | O | |
| 125 | H | H | F | H | $CF_3$ | 4-F | $C_4H_9$-n | O | |
| 126 | H | H | F | H | $CF_3$ | H | $C_4H_9$-n | O | |
| 127 | H | H | F | H | $CF_3$ | 4-F | $C_4H_9$-i | O | |
| 128 | H | H | F | H | $CF_3$ | H | $C_4H_9$-i | S | |
| 129 | H | H | F | H | $CF_3$ | 4-F | $C_4H_9$-i | S | |
| 130 | H | H | F | H | $CF_3$ | H | $C_4H_9$-i | O | |
| 131 | H | H | F | H | $CF_3$ | 4-F | $C_4H_9$-s | O | |
| 132 | H | H | F | H | $CF_3$ | H | $C_4H_9$-s | O | |
| 133 | H | H | F | H | $CF_3$ | 4-F | $C_4H_9$-t | O | |
| 134 | H | H | F | H | $CF_3$ | H | $C_4H_9$-t | O | |
| 135 | H | H | Cl | Cl | $CF_3$ | 4-F | $C_2H_5$ | O | m.p. 59–60 |
| 136 | H | H | Cl | Cl | $CF_3$ | H | $C_2H_5$ | O | |
| 137 | H | H | Cl | H | $CF_3$ | 4-F | $CH_3$ | O | See Table 3 |
| 138 | H | H | Cl | H | $CF_3$ | H | $CH_3$ | O | See Table 3 |
| 139 | H | H | Cl | H | $CF_3$ | 4-F | $C_2H_5$ | O | See Table 3 |
| 140 | H | H | Cl | H | $CF_3$ | H | $C_2H_5$ | O | See Table 3 |
| 141 | H | H | Cl | H | $CF_3$ | 4-F | $C_3H_7$-n | O | See Table 3 |
| 142 | H | H | Cl | H | $CF_3$ | H | $C_3H_7$-n | O | See Table 3 |
| 143 | H | H | Cl | H | $CF_3$ | 4-F | $C_4H_9$-i | O | |
| 144 | H | H | Cl | H | $CF_3$ | H | $C_4H_9$-i | O | |
| 145 | H | H | Cl | H | $CF_3$ | 4-F | $C_4H_9$-i | O | |
| 146 | H | H | Cl | H | $CF_3$ | H | $C_4H_9$-i | O | |
| 147 | H | H | Cl | H | $CF_3$ | 4-F | $C_4H_9$-s | O | |
| 148 | H | H | Cl | H | $CF_3$ | H | $C_4H_9$-s | O | |
| 149 | H | H | Cl | H | $CF_3$ | 4-F | $C_4H_9$-t | O | |
| 150 | H | H | Cl | H | $CF_3$ | H | $C_4H_9$-t | O | |
| 151 | H | H | Cl | H | $CF_3$ | 4-F | $CH_3$ | S | |
| 152 | H | H | Cl | H | $CF_3$ | H | $CH_3$ | S | |
| 153 | H | H | Cl | H | $CF_3$ | 4-F | $C_2H_5$ | S | |
| 154 | H | H | Cl | H | $CF_3$ | H | $C_2H_5$ | S | See Table 3 |
| 155 | H | H | Cl | H | $CF_3$ | 4-F | $C_3H_7$-n | S | |
| 156 | H | H | Cl | H | $CF_3$ | H | $C_3H_7$-n | S | |
| 157 | H | H | Cl | H | $CF_3$ | 4-F | $CH_3$ | $SO_2$ | |
| 158 | H | H | Cl | H | $CF_3$ | H | $CH_3$ | $SO_2$ | |
| 159 | H | H | Cl | H | $CF_3$ | 4-F | $C_2H_5$ | $SO_2$ | |
| 160 | H | H | Cl | H | $CF_3$ | H | $C_2H_5$ | $SO_2$ | See Table 3 |
| 161 | H | H | Cl | H | $CF_3$ | 4-F | $C_3H_7$-n | $SO_2$ | |
| 162 | H | H | Cl | H | $CF_3$ | H | $C_3H_7$-n | $SO_2$ | |
| 163 | H | H | Br | H | $CF_3$ | 4-F | $CH_3$ | O | |
| 164 | H | H | Br | H | $CF_3$ | H | $CH_3$ | O | |

TABLE 1-continued

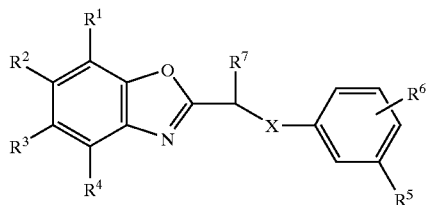

(1)

| Compound | R$^1$ | R$^2$ | R$^3$ | R$^4$ | R$^5$ | R$^6$ | R$^7$ | X | Physical property |
|---|---|---|---|---|---|---|---|---|---|
| 165 | H | H | Br | H | CF$_3$ | 4-F | C$_2$H$_5$ | O | See Table 3 |
| 166 | H | H | Br | H | CF$_3$ | H | C$_2$H$_5$ | O | See Table 3 |
| 167 | H | H | Br | H | CF$_3$ | 4-F | C$_3$H$_7$-n | O | |
| 168 | H | H | Br | H | CF$_3$ | H | C$_3$H$_7$-n | O | |
| 169 | H | H | I | H | CF$_3$ | 4-F | CH$_3$ | O | |
| 170 | H | H | I | H | CF$_3$ | H | CH$_3$ | O | |
| 171 | H | H | I | H | CF$_3$ | 4-F | C$_2$H$_5$ | O | See Table 3 |
| 172 | H | H | I | H | CF$_3$ | H | C$_2$H$_5$ | O | See Table 3 |
| 173 | H | H | I | H | CF$_3$ | 4-F | C$_3$H$_7$-n | O | |
| 174 | H | H | I | H | CF$_3$ | H | C$_3$H$_7$-n | O | |
| 175 | H | H | NO$_2$ | H | CF$_3$ | 4-F | CH$_3$ | O | |
| 176 | H | H | NO$_2$ | H | CF$_3$ | H | CH$_3$ | O | See Table 3 |
| 177 | H | H | NO$_2$ | H | CF$_3$ | 4-F | C$_2$H$_5$ | O | See Table 3 |
| 178 | H | H | NO$_2$ | H | CF$_3$ | H | C$_2$H$_5$ | O | See Table 3 |
| 179 | H | H | NO$_2$ | H | CF$_3$ | 4-F | C$_3$H$_7$-n | O | |
| 180 | H | H | NO$_2$ | H | CF$_3$ | H | C$_3$H$_7$-n | O | |
| 181 | H | H | CH$_3$ | H | CF$_3$ | 4-F | CH$_3$ | O | |
| 182 | H | H | CH$_3$ | H | CF$_3$ | H | CH$_3$ | O | |
| 183 | H | H | CH$_3$ | H | CF$_3$ | 4-F | C$_2$H$_5$ | O | See Table 3 |
| 184 | H | H | CH$_3$ | H | CF$_3$ | H | C$_2$H$_5$ | O | |
| 185 | H | H | CH$_3$ | H | CF$_3$ | 4-F | C$_3$H$_7$-n | O | |
| 186 | H | H | CH$_3$ | H | CF$_3$ | H | C$_3$H$_7$-n | O | |
| 187 | H | H | CN | H | CF$_3$ | 4-F | CH$_3$ | O | |
| 188 | H | H | CN | H | CF$_3$ | H | CH$_3$ | O | |
| 189 | H | H | CN | H | CF$_3$ | 4-F | C$_2$H$_5$ | O | See Table 3 |
| 190 | H | H | CN | H | CF$_3$ | H | C$_2$H$_5$ | O | See Table 3 |
| 191 | H | H | CN | H | CF$_3$ | 4-F | C$_3$H$_7$-n | O | See Table 3 |
| 192 | H | H | CN | H | CF$_3$ | H | C$_3$H$_7$-n | O | See Table 3 |
| 193 | H | H | CN | H | CF$_3$ | 4-F | C$_3$H$_7$-i | O | See Table 3 |
| 194 | H | H | CN | H | CF$_3$ | H | C$_3$H$_7$-i | O | |
| 195 | H | H | CF$_3$ | H | CF$_3$ | 4-F | CH$_3$ | O | |
| 196 | H | H | CF$_3$ | H | CF$_3$ | H | CH$_3$ | O | |
| 197 | H | H | CF$_3$ | H | CF$_3$ | 4-F | C$_2$H$_5$ | O | See Table 3 |
| 198 | H | H | CF$_3$ | H | CF$_3$ | H | C$_2$H$_5$ | O | See Table 3 |
| 199 | H | H | CF$_3$ | H | CF$_3$ | 4-F | C$_3$H$_7$-n | O | See Table 3 |
| 200 | H | H | CF$_3$ | H | CF$_3$ | H | C$_3$H$_7$-n | O | See Table 3 |
| 201 | H | H | CH$_3$S | H | CF$_3$ | 4-F | CH$_3$ | O | |
| 202 | H | H | CH$_3$S | H | CF$_3$ | H | CH$_3$ | O | |
| 203 | H | H | CH$_3$S | H | CF$_3$ | 4-F | C$_2$H$_5$ | O | |
| 204 | H | H | CH$_3$S | H | CF$_3$ | H | C$_2$H$_5$ | O | |
| 205 | H | H | CH$_3$S | H | CF$_3$ | 4-F | C$_3$H$_7$-n | O | |
| 206 | H | H | CH$_3$S | H | CF$_3$ | H | C$_3$H$_7$-n | O | |
| 207 | H | H | CH$_3$SO | H | CF$_3$ | 4-F | CH$_3$ | O | |
| 208 | H | H | CH$_3$SO | H | CF$_3$ | H | CH$_3$ | O | |
| 209 | H | H | CH$_3$SO | H | CF$_3$ | 4-F | C$_2$H$_5$ | O | |
| 210 | H | H | CH$_3$SO | H | CF$_3$ | H | C$_2$H$_5$ | O | |

TABLE 1-continued

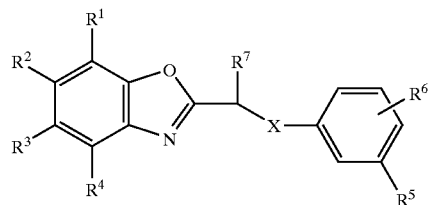

(1)

| Compound | R¹ | R² | R³ | R⁴ | R⁵ | R⁶ | R⁷ | X | Physical property |
|---|---|---|---|---|---|---|---|---|---|
| 211 | H | H | CH₃SO | H | CF₃ | 4-F | C₃H₇-n | O | |
| 212 | H | H | CH₃SO | H | CF₃ | H | C₃H₇-n | O | |
| 213 | H | H | CH₃SO₂ | H | CF₃ | 4-F | CH₃ | O | |
| 214 | H | H | CH₃SO₂ | H | CF₃ | H | CH₃ | O | |
| 215 | H | H | CH₃SO₂ | H | CF₃ | 4-F | C₂H₅ | O | See Table 3 |
| 216 | H | H | CH₃SO₂ | H | CF₃ | H | C₂H₅ | O | See Table 3 |
| 217 | H | H | CH₃SO₂ | H | CF₃ | 4-F | C₃H₇-n | O | See Table 3 |
| 218 | H | H | CH₃SO₂ | H | CF₃ | H | C₃H₇-n | O | See Table 3 |
| 219 | H | H | C₂H₅SO₂ | H | CF₃ | 4-F | CH₃ | O | |
| 220 | H | H | C₂H₅SO₂ | H | CF₃ | H | CH₃ | O | |
| 221 | H | H | C₂H₅SO₂ | H | CF₃ | 4-F | C₂H₅ | O | See Table 3 |
| 222 | H | H | C₂H₅SO₂ | H | CF₃ | H | C₂H₅ | O | |
| 223 | H | H | C₂H₅SO₂ | H | CF₃ | 4-F | C₃H₇-n | O | |
| 224 | H | H | C₂H₅SO₂ | H | CF₃ | H | C₃H₇-n | O | |
| 225 | H | H | CF₃O | H | CF₃ | 4-F | CH₃ | O | |
| 226 | H | H | CF₃O | H | CF₃ | H | CH₃ | O | |
| 227 | H | H | CF₃O | H | CF₃ | 4-F | C₂H₅ | O | See Table 3 |
| 228 | H | H | CF₃O | H | CF₃ | H | C₂H₅ | O | See Table 3 |
| 229 | H | H | CF₃O | H | CF₃ | 4-F | C₃H₇-n | O | |
| 230 | H | H | CF₃O | H | CF₃ | H | C₃H₇-n | O | |
| 231 | H | H | C₂H₅OCO | H | CF₃ | 4-F | CH₃ | O | |
| 232 | H | H | C₂H₅OCO | H | CF₃ | H | CH₃ | O | |
| 233 | H | H | C₂H₅OCO | H | CF₃ | 4-F | C₂H₅ | O | See Table 3 |
| 234 | H | H | C₂H₅OCO | H | CF₃ | 4-F | C₂H₅ | O | See Table 3 |
| 235 | H | H | C₂H₅OCO | H | CF₃ | 4-F | C₃H₇-n | O | |
| 236 | H | H | C₂H₅OCO | H | CF₃ | 4-F | C₃H₇-n | O | |
| 237 | H | H | COOH | H | CF₃ | 4-F | CH₃ | O | |
| 238 | H | H | COOH | H | CF₃ | H | CH₃ | O | |
| 239 | H | H | COOH | H | CF₃ | 4-F | C₂H₅ | O | m.p. 243–245 |
| 240 | H | H | COOH | H | CF₃ | H | C₂H₅ | O | See Table 3 |
| 241 | H | H | COOH | H | CF₃ | 4-F | C₃H₇-n | O | |
| 242 | H | H | COOH | H | CF₃ | H | C₃H₇-n | O | |
| 243 | H | H | CH₃CONH | H | CF₃ | 4-F | CH₃ | O | |
| 244 | H | H | CH₃CONH | H | CF₃ | H | CH₃ | O | |
| 245 | H | H | CH₃CONH | H | CF₃ | 4-F | C₂H₅ | O | See Table 3 |
| 246 | H | H | CH₃CONH | H | CF₃ | H | C₂H₅ | O | |
| 247 | H | H | CH₃CONH | H | CF₃ | 4-F | C₃H₇-n | O | |
| 248 | H | H | CH₃CONH | H | CF₃ | H | C₃H₇-n | O | |
| 249 | H | H | CN | H | CF₃ | 4-F | CH₃ | S | |
| 250 | H | H | CN | H | CF₃ | H | CH₃ | S | |
| 251 | H | H | CN | H | CF₃ | 4-F | C₂H₅ | S | |
| 252 | H | H | CN | H | CF₃ | H | C₂H₅ | S | See Table 3 |
| 253 | H | H | CN | H | CF₃ | 4-F | C₃H₇-n | S | |
| 254 | H | H | CN | H | CF₃ | H | C₃H₇-n | S | |
| 255 | H | H | CF₃ | H | CF₃ | 4-F | CH₃ | S | |
| 256 | H | H | CF₃ | H | CF₃ | H | CH₃ | S | |
| 257 | H | H | CF₃ | H | CF₃ | 4-F | C₂H₅ | S | |
| 258 | H | H | CF₃ | H | CF₃ | H | C₂H₅ | S | See Table 3 |
| 259 | H | H | CF₃ | H | CF₃ | 4-F | C₃H₇-n | S | |
| 260 | H | H | CF₃ | H | CF₃ | H | C₃H₇-n | S | |

TABLE 1-continued

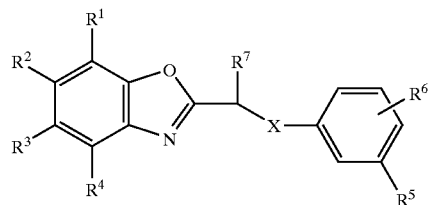

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 261 | H | H | CN | H | $CF_3$ | 4-F | $CH_3$ | $SO_2$ | |
| 262 | H | H | CN | H | $CF_3$ | H | $CH_3$ | $SO_2$ | |
| 263 | H | H | CN | H | $CF_3$ | 4-F | $C_2H_5$ | $SO_2$ | |
| 264 | H | H | CN | H | $CF_3$ | H | $C_2H_5$ | $SO_2$ | See Table 3 |
| 265 | H | H | CN | H | $CF_3$ | 4-F | $C_3H_7$-n | $SO_2$ | |
| 266 | H | H | CN | H | $CF_3$ | H | $C_3H_7$-n | $SO_2$ | |
| 267 | H | H | $CF_3$ | H | $CF_3$ | 4-F | $CH_3$ | $SO_2$ | |
| 268 | H | H | $CF_3$ | H | $CF_3$ | H | $CH_3$ | $SO_2$ | |
| 269 | H | H | $CF_3$ | H | $CF_3$ | 4-F | $C_2H_5$ | $SO_2$ | |
| 270 | H | H | $CF_3$ | H | $CF_3$ | H | $C_2H_5$ | $SO_2$ | See Table 3 |
| 271 | H | H | $CF_3$ | H | $CF_3$ | 4-F | $C_3H_7$-n | $SO_2$ | |
| 272 | H | H | $CF_3$ | H | $CF_3$ | H | $C_3H_7$-n | $SO_2$ | |
| 273 | H | H | $CF_3$ | H | $CF_3$ | 4-F | $CH_3$ | SO | |
| 274 | H | H | $CF_3$ | H | $CF_3$ | H | $CH_3$ | SO | |
| 275 | H | H | $CF_3$ | H | $CF_3$ | 4-F | $C_2H_5$ | SO | |
| 276 | H | H | $CF_3$ | H | $CF_3$ | H | $C_2H_5$ | SO | |
| 277 | H | F | F | H | $CF_3$ | H | $C_4H_9$-i | O | |
| 278 | H | F | F | H | $CF_3$ | 4-F | $C_4H_9$-i | O | |
| 279 | H | F | F | H | $CF_3$ | H | $CH_3$ | S | |
| 280 | H | F | F | H | $CF_3$ | 4-F | $CH_3$ | S | |
| 281 | H | F | F | H | $CF_3$ | H | $CH_3$ | O | |
| 282 | H | F | F | H | $CF_3$ | 4-F | $CH_3$ | O | |
| 283 | H | F | F | H | $CF_3$ | H | $C_2H_5$ | O | See Table 3 |
| 284 | H | F | F | H | $CF_3$ | 4-F | $C_2H_5$ | O | See Table 3 |
| 285 | H | F | F | H | $CF_3$ | H | $C_3H_7$-n | O | See Table 3 |
| 286 | H | F | F | H | $CF_3$ | 4-F | $C_3H_7$-n | O | See Table 3 |
| 287 | H | F | F | H | $CF_3$ | H | $C_3H_7$-i | O | |
| 288 | H | F | F | H | $CF_3$ | 4-F | $C_3H_7$-i | O | |
| 289 | H | F | Cl | H | $CF_3$ | H | $CH_3$ | O | |
| 290 | H | F | Cl | H | $CF_3$ | 4-F | $CH_3$ | O | |
| 291 | H | F | Cl | H | $CF_3$ | H | $C_2H_5$ | O | See Table 3 |
| 292 | H | F | Cl | H | $CF_3$ | 4-F | $C_2H_5$ | O | See Table 3 |
| 293 | H | F | Cl | H | $CF_3$ | H | $C_3H_7$-n | O | See Table 3 |
| 294 | H | F | Cl | H | $CF_3$ | 4-F | $C_3H_7$-n | O | See Table 3 |
| 295 | H | Cl | Cl | H | $CF_3$ | H | $CH_3$ | O | |
| 296 | H | Cl | Cl | H | $CF_3$ | 4-F | $CH_3$ | O | |
| 297 | H | Cl | Cl | H | $CF_3$ | H | $C_2H_5$ | O | |
| 298 | H | Cl | Cl | H | $CF_3$ | 4-F | $C_2H_5$ | O | See Table 3 |
| 299 | H | Cl | Cl | H | $CF_3$ | H | $C_3H_7$-n | O | |
| 300 | H | Cl | Cl | H | $CF_3$ | 4-F | $C_3H_7$-n | O | See Table 3 |
| 301 | H | CN | Cl | H | $CF_3$ | H | $CH_3$ | O | |
| 302 | H | CN | Cl | H | $CF_3$ | 4-F | $CH_3$ | O | |
| 303 | H | CN | Cl | H | $CF_3$ | H | $C_2H_5$ | O | |
| 304 | H | CN | Cl | H | $CF_3$ | 4-F | $C_2H_5$ | O | |
| 305 | H | CN | Cl | H | $CF_3$ | H | $C_3H_7$-n | O | |
| 306 | H | CN | Cl | H | $CF_3$ | 4-F | $C_3H_7$-n | O | |
| 307 | H | CN | F | H | $CF_3$ | H | $CH_3$ | O | |
| 308 | H | CN | F | H | $CF_3$ | 4-F | $CH_3$ | O | |
| 309 | H | CN | F | H | $CF_3$ | H | $C_2H_5$ | O | |
| 310 | H | CN | F | H | $CF_3$ | 4-F | $C_2H_5$ | O | |
| 311 | H | CN | F | H | $CF_3$ | H | $C_3H_7$-n | O | |

TABLE 1-continued

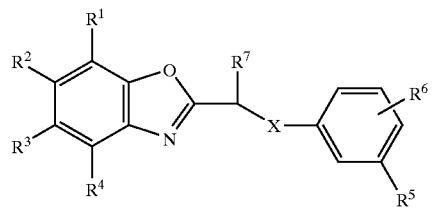

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 312 | H | CN | F | H | $CF_3$ | 4-F | $C_3H_7$-n | O | |
| 313 | H | CN | CN | H | $CF_3$ | H | $CH_3$ | O | |
| 314 | H | CN | CN | H | $CF_3$ | 4-F | $CH_3$ | O | |
| 315 | H | CN | CN | H | $CF_3$ | H | $C_2H_5$ | O | See Table 3 |
| 316 | H | CN | CN | H | $CF_3$ | 4-F | $C_2H_5$ | O | |
| 317 | H | CN | CN | H | $CF_3$ | H | $C_3H_7$-n | O | See Table 3 |
| 318 | H | CN | CN | H | $CF_3$ | 4-F | $C_3H_7$-n | O | |
| 319 | H | F | $CF_3$ | H | $CF_3$ | H | $CH_3$ | O | |
| 320 | H | F | $CF_3$ | H | $CF_3$ | 4-F | $CH_3$ | O | |
| 321 | H | F | $CF_3$ | H | $CF_3$ | H | $C_2H_5$ | O | |
| 322 | H | F | $CF_3$ | H | $CF_3$ | 4-F | $C_2H_5$ | O | |
| 323 | H | F | $CF_3$ | H | $CF_3$ | H | $C_3H_5$-n | O | |
| 324 | H | F | $CF_3$ | H | $CF_3$ | 4-F | $C_3H_5$-n | O | |
| 325 | H | $NO_2$ | $CF_3$ | H | $CF_3$ | H | $CH_3$ | O | |
| 326 | H | $NO_2$ | $CF_3$ | H | $CF_3$ | 4-F | $CH_3$ | O | |
| 327 | H | $NO_2$ | $CF_3$ | H | $CF_3$ | H | $C_2H_5$ | O | |
| 328 | H | $NO_2$ | $CF_3$ | H | $CF_3$ | 4-F | $C_2H_5$ | O | |
| 329 | H | $NO_2$ | $CF_3$ | H | $CF_3$ | H | $C_3H_7$-n | O | |
| 330 | H | $NO_2$ | $CF_3$ | H | $CF_3$ | 4-F | $C_3H_7$-n | O | |
| 331 | H | $NO_2$ | Cl | H | $CF_3$ | H | $CH_3$ | O | |
| 332 | H | $NO_2$ | Cl | H | $CF_3$ | 4-F | $CH_3$ | O | |
| 333 | H | $NO_2$ | Cl | H | $CF_3$ | H | $C_2H_5$ | O | |
| 334 | H | $NO_2$ | Cl | H | $CF_3$ | 4-F | $C_2H_5$ | O | See Table 3 |
| 335 | H | $NO_2$ | Cl | H | $CF_3$ | H | $C_3H_7$-n | O | |
| 336 | H | $NO_2$ | Cl | H | $CF_3$ | 4-F | $C_3H_7$-n | O | |
| 337 | H | $CH_3$ | Cl | H | $CF_3$ | H | $CH_3$ | O | |
| 338 | H | $CH_3$ | Cl | H | $CF_3$ | 4-F | $CH_3$ | O | |
| 339 | H | $CH_3$ | Cl | H | $CF_3$ | H | $C_2H_5$ | O | See Table 3 |
| 340 | H | $CH_3$ | Cl | H | $CF_3$ | 4-F | $C_2H_5$ | O | See Table 3 |
| 341 | H | $CH_3$ | Cl | H | $CF_3$ | H | $C_3H_5$-n | O | |
| 342 | H | $CH_3$ | Cl | H | $CF_3$ | 4-F | $C_3H_7$-n | O | See Table 3 |
| 343 | H | F | CN | H | $CF_3$ | H | $CH_3$ | O | |
| 344 | H | F | CN | H | $CF_3$ | 4-F | $CH_3$ | O | |
| 345 | H | F | CN | H | $CF_3$ | H | $C_2H_5$ | O | See Table 3 |
| 346 | H | F | CN | H | $CF_3$ | 4-F | $C_2H_5$ | O | See Table 3 |
| 347 | H | F | CN | H | $CF_3$ | H | $C_3H_7$-n | O | See Table 3 |
| 348 | H | F | CN | H | $CF_3$ | 4-F | $C_3H_7$-n | O | See Table 3 |
| 349 | H | H | F | H | CN | H | $CH_3$ | O | |
| 350 | H | H | F | H | CN | H | $C_2H_5$ | O | |
| 351 | H | H | F | H | CN | H | $C_3H_5$-n | O | |
| 352 | H | H | Cl | H | CN | H | $CH_3$ | O | |
| 353 | H | H | Cl | H | CN | H | $C_2H_5$ | O | See Table 3 |
| 354 | H | H | Cl | H | CN | H | $C_3H_7$-n | O | |
| 355 | H | H | Cl | H | $CH_3S$ | H | $CH_3$ | O | |
| 356 | H | H | Cl | H | $CH_3S$ | H | $C_2H_5$ | O | |
| 357 | H | H | Cl | H | $CH_3S$ | H | $C_3H_7$-n | O | |
| 358 | H | H | Cl | H | $CH_3SO$ | H | $CH_3$ | O | |
| 359 | H | H | Cl | H | $CH_3SO$ | H | $C_2H_5$ | O | |
| 360 | H | H | Cl | H | $CH_3SO$ | H | $C_3H_7$-n | O | |
| 361 | H | H | Cl | H | $CH_3SO_2$ | H | $CH_3$ | O | |
| 362 | H | H | Cl | H | $CH_3SO_2$ | H | $C_2H_5$ | O | See Table 3 |

TABLE 1-continued

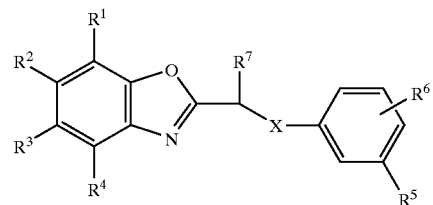

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 363 | H | H | Cl | H | $CH_3SO_2$ | H | $C_3H_7$-n | O | See Table 3 |
| 364 | H | H | Cl | H | $NO_2$ | H | $CH_3$ | O | |
| 365 | H | H | Cl | H | $NO_2$ | H | $C_2H_5$ | O | |
| 366 | H | H | Cl | H | $NO_2$ | H | $C_3H_7$-n | O | |
| 367 | H | H | Cl | H | CN | 4-CN | $CH_3$ | O | |
| 368 | H | H | Cl | H | CN | 4-CN | $C_2H_5$ | O | See Table 3 |
| 369 | H | H | Cl | H | CN | 4-CN | $C_3H_7$-n | O | See Table 3 |
| 370 | H | H | Cl | H | CN | H | $CH_3$ | S | |
| 371 | H | H | Cl | H | CN | H | $C_2H_5$ | S | |
| 372 | H | H | Cl | H | CN | H | $C_3H_7$-n | S | |
| 373 | H | H | Cl | H | CN | H | $C_3H_7$-i | O | See Table 3 |
| 374 | H | H | Cl | H | CN | 4-CN | $CH_3$ | S | |
| 375 | H | H | Cl | H | CN | 4-CN | $C_2H_5$ | S | |
| 376 | H | H | Cl | H | CN | 4-CN | $C_3H_7$-n | S | |
| 377 | H | H | Cl | H | CN | 4-CN | $C_3H_7$-i | O | See Table 3 |
| 378 | H | H | Cl | H | $CH_3SO_2$ | 4-F | $CH_3$ | O | |
| 379 | H | H | Cl | H | $CH_3SO_2$ | 4-F | $C_2H_5$ | O | |
| 380 | H | H | Cl | H | $CH_3SO_2$ | 4-F | $C_3H_7$-n | O | |
| 381 | H | H | Cl | H | $CH_3SO_2$ | H | $C_3H_7$-i | O | See Table 3 |
| 382 | H | H | $CF_3$ | H | CN | H | $CH_3$ | O | |
| 383 | H | H | $CF_3$ | H | CN | H | $C_2H_5$ | O | See Table 3 |
| 384 | H | H | $CF_3$ | H | CN | H | $C_3H_7$-n | O | See Table 3 |
| 385 | H | H | $CF_3$ | H | CN | H | $C_3H_7$-i | O | See Table 3 |
| 386 | H | H | $CF_3$ | H | CN | H | Ph | O | See Table 3 |
| 387 | H | H | $CF_3$ | H | CN | 4-CN | $CH_3$ | O | |
| 388 | H | H | $CF_3$ | H | CN | 4-CN | $C_2H_5$ | O | See Table 3 |
| 389 | H | H | $CF_3$ | H | CN | 4-CN | $C_3H_7$-n | O | See Table 3 |
| 390 | H | H | $CF_3$ | H | CN | 4-CN | $C_3H_7$-i | O | See Table 3 |
| 391 | H | H | CN | H | CN | H | $CH_3$ | O | |
| 392 | H | H | CN | H | CN | H | $C_2H_5$ | O | See Table 3 |
| 393 | H | H | CN | H | CN | H | $C_3H_7$-n | O | See Table 3 |
| 394 | H | H | CN | H | CN | H | $C_3H_7$-i | O | m.p. 200–202 |
| 395 | H | H | CN | H | $CF_3O$ | H | $CH_3$ | O | |
| 396 | H | H | CN | H | $CF_3O$ | H | $C_2H_5$ | O | See Table 3 |
| 397 | H | H | CN | H | $CF_3O$ | H | $C_3H_5$-n | O | |
| 398 | H | H | CN | H | CN | 4-CN | $CH_3$ | O | |
| 399 | H | H | CN | H | CN | 4-CN | $C_2H_5$ | O | |
| 400 | H | H | CN | H | CN | 4-CN | $C_3H_7$-n | O | See Table 3 |
| 401 | H | H | CN | H | CN | 4-CN | $C_3H_7$-i | O | See Table 3 |
| 402 | H | H | CN | H | $CH_3SO_2$ | H | $CH_3$ | O | |
| 403 | H | H | CN | H | $CH_3SO_2$ | H | $C_2H_5$ | O | See Table 3 |
| 404 | H | H | CN | H | $CH_3SO_2$ | H | $C_3H_7$-n | O | See Table 3 |
| 405 | H | H | CN | H | $CH_3SO_2$ | H | $C_3H_7$-i | O | See |

TABLE 1-continued

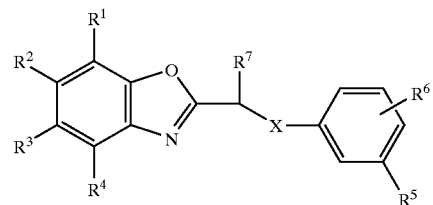

(1)

| Compound | R¹ | R² | R³ | R⁴ | R⁵ | R⁶ | R⁷ | X | Physical property |
|---|---|---|---|---|---|---|---|---|---|
| 406 | H | H | CF₃ | H | CH₃SO₂ | H | CH₃ | O | Table 3 |
| 407 | H | H | CF₃ | H | CH₃SO₂ | H | C₂H₅ | O | |
| 408 | H | H | CF₃ | H | CH₃SO₂ | H | C₃H₇-n | O | See Table 3 |
| 409 | H | H | CF₃ | H | CH₃SO₂ | H | C₃H₇-i | O | See Table 3 |
| 410 | H | F | F | H | CN | H | CH₃ | O | |
| 411 | H | F | F | H | CN | H | C₂H₅ | O | See Table 3 |
| 412 | H | F | F | H | CN | H | C₃H₇-n | O | See Table 3 |
| 413 | H | F | Cl | H | CN | H | CH₃ | O | |
| 414 | H | F | Cl | H | CN | H | C₂H₅ | O | See Table 3 |
| 415 | H | F | Cl | H | CN | H | C₃H₇-n | O | See Table 3 |
| 416 | H | F | Cl | H | CN | 4-CN | CH₃ | O | |
| 417 | H | F | Cl | H | CN | 4-CN | C₂H₅ | O | See Table 3 |
| 418 | H | F | Cl | H | CN | 4-CN | C₃H₇-n | O | See Table 3 |
| 419 | H | F | Cl | H | CH₃SO₂ | 4-CN | CH₃ | O | |
| 420 | H | F | Cl | H | CH₃SO₂ | H | C₂H₅ | O | See Table 3 |
| 421 | H | F | Cl | H | CH₃SO₂ | H | C₃H₇-n | O | See Table 3 |
| 422 | H | F | CN | H | CN | H | CH₃ | O | |
| 423 | H | F | CN | H | CN | H | C₂H₅ | O | See Table 3 |
| 424 | H | F | CN | H | CN | H | C₃H₇-n | O | See Table 3 |
| 425 | H | H | Cl | H | H | 4-CF₃ | CH₃ | O | |
| 426 | H | H | Cl | H | H | 4-CF₃ | C₂H₅ | O | See Table 3 |
| 427 | H | H | Cl | H | H | 4-CF₃ | C₃H₇-n | O | |
| 428 | H | F | CF₃ | H | H | 4-CN | CH₃ | O | |
| 429 | H | F | CF₃ | H | H | 4-CN | C₂H₅ | O | m.p. 92–93 |
| 430 | H | F | CF₃ | H | H | 4-CN | C₃H₇-n | O | |
| 431 | H | H | NO₂ | H | CF₃ | 4-Cl | CH₃ | O | |
| 432 | H | H | NO₂ | H | CF₃ | 4-Cl | C₂H₅ | O | See Table 3 |
| 433 | H | H | NO₂ | H | CF₃ | 4-Cl | C₃H₇-n | O | |
| 434 | H | H | NO₂ | H | H | H | CH₃ | O | |
| 435 | H | H | NO₂ | H | H | H | C₂H₅ | O | See Table 3 |
| 436 | H | H | NO₂ | H | H | H | C₃H₇-n | O | |
| 437 | H | H | Cl | H | CF₃ | 4-Cl | CH₃ | O | |
| 438 | H | H | Cl | H | CF₃ | 4-Cl | C₂H₅ | O | See Table 3 |
| 439 | H | H | Cl | H | CF₃ | 4-Cl | C₃H₇-n | O | |
| 440 | H | H | F | H | CF₃ | 4-Cl | CH₃ | O | |
| 441 | H | H | F | H | CF₃ | 4-Cl | C₂H₅ | O | See Table 3 |
| 442 | H | H | F | H | CF₃ | 4-Cl | C₃H₇-n | O | |
| 443 | H | H | CF₃O | H | CF₃ | 4-Cl | CH₃ | O | |
| 444 | H | H | CF₃O | H | CF₃ | 4-Cl | C₂H₅ | O | See Table 3 |
| 445 | H | H | CF₃O | H | CF₃ | 4-Cl | C₃H₇-n | O | |
| 446 | H | H | Cl | H | CF₃O | H | CH₃ | O | |
| 447 | H | H | Cl | H | CF₃O | H | C₂H₅ | O | See Table 3 |
| 448 | H | H | Cl | H | CF₃O | H | C₃H₇-n | O | |

TABLE 1-continued

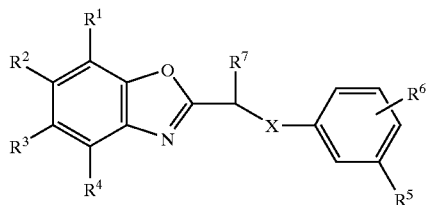

(1)

| Compound | $R^1$ | $R^2$ | $R^3$ | $R^4$ | $R^5$ | $R^6$ | $R^7$ | X | Physical property |
|---|---|---|---|---|---|---|---|---|---|
| 449 | H | H | $NO_2$ | H | $CF_3O$ | H | $CH_3$ | O | |
| 450 | H | H | $NO_2$ | H | $CF_3O$ | H | $C_2H_5$ | O | See Table 3 |
| 451 | H | H | $NO_2$ | H | $CF_3O$ | H | $C_3H_7$-n | O | |
| 452 | H | H | $CF_3$ | H | H | 4-Cl | $CH_3$ | O | |
| 453 | H | H | $CF_3$ | H | H | 4-Cl | $C_2H_5$ | O | See Table 3 |
| 454 | H | H | $CF_3$ | H | H | 4-Cl | $C_3H_7$-n | O | |
| 455 | H | CN | Cl | H | CN | H | $CH_3$ | O | |
| 456 | H | CN | Cl | H | CN | H | $C_2H_5$ | O | |
| 457 | H | H | Cl | H | CN | H | $C_3H_7$-n | O | See Table 3 |
| 458 | H | F | F | H | CN | 4-CN | $CH_3$ | O | |
| 459 | H | F | F | H | CN | 4-CN | $C_2H_5$ | O | See Table 3 |
| 460 | H | F | F | H | CN | 4-CN | $C_3H_7$-n | O | See Table 3 |
| 461 | H | F | F | H | $CH_3SO_2$ | H | $CH_3$ | O | |
| 462 | H | F | F | H | $CH_3SO_2$ | H | $C_2H_5$ | O | See Table 3 |
| 463 | H | F | F | H | $CH_3SO$ | H | $C_3H_7$-n | O | See Table 3 |
| 464 | H | F | CN | H | CN | 4-CN | $CH_3$ | O | |
| 465 | H | F | CN | H | CN | 4-CN | $C_2H_5$ | O | See Table 3 |
| 466 | H | F | CN | H | CN | 4-CN | $C_3H_7$-n | O | See Table 3 |
| 467 | H | F | CN | H | $CH_3SO_2$ | H | $CH_3$ | O | |
| 468 | H | F | CN | H | $CH_3SO_2$ | H | $C_2H_5$ | O | See Table 3 |
| 469 | H | F | CN | H | $CH_3SO_2$ | H | $C_3H_7$-n | O | See Table 3 |
| 470 | H | F | F | H | CN | 4-F | $C_2H_5$ | O | |
| 471 | H | $CF_3$ | F | H | $CF_3$ | H | $C_2H_5$ | O | See Table 3 |
| 472 | H | $CF_3$ | F | H | $CF_3$ | 4-F | $C_2H_5$ | O | |
| 473 | H | $CF_3$ | F | H | $CF_3$ | H | CH3 | O | |
| 474 | H | $CF_3$ | F | H | $CF_3$ | H | $C_3H_7$-n | O | See Table 3 |
| 475 | H | $CF_3$ | F | H | $CF_3$ | 4-F | $C_3H_7$-n | O | |
| 476 | H | H | Cl | H | $CF_3$ | 4-F | $C_4H_9$-n | O | See Table 3 |
| 477 | H | H | Cl | H | $CF_3$ | H | $C_4H_9$-n | O | |
| 478 | H | H | Cl | H | H | 4-F | $C_2H_5$ | O | |
| 479 | H | H | Cl | H | H | H | $C_4H_9$-n | O | See Table 3 |
| 480 | H | H | Cl | H | CN | 4-F | $CH_3$ | O | |
| 481 | H | $CH_3$ | Cl | H | CN | H | $C_2H_5$ | O | See Table 3 |
| 482 | H | $CH_3$ | Cl | H | CN | 4-F | $C_2H_5$ | O | |
| 483 | H | $CH_3$ | Cl | H | CN | H | $CH_3$ | O | |
| 484 | H | $CH_3$ | Cl | H | CN | H | $C_3H_7$-n | O | See Table 3 |
| 485 | H | $CH_3$ | Cl | H | CN | 4-F | $C_3H_7$-n | O | |
| 486 | H | Cl | F | H | $CF_3$ | 4-F | $CH_3$ | O | |
| 487 | H | $CH_3$ | $CH_3SO_2$ | H | $CF_3$ | 4-F | $C_2H_5$ | O | See Table 3 |
| 488 | H | $CH_3$ | $CH_3SO_2$ | H | $CF_3$ | 4-F | $C_3H_7$-n | O | |
| 489 | H | $CH_3$ | $CH_3SO_2$ | H | $CF_3$ | H | $C_3H_7$-n | O | See Table 3 |
| 490 | H | $CH_3$ | $CH_3SO_2$ | H | $CF_3$ | H | $C_2H_5$ | O | See Table 3 |
| 491 | H | $CH_3$ | $CH_3SO_2$ | H | CN | H | $C_2H_5$ | O | See |

TABLE 1-continued

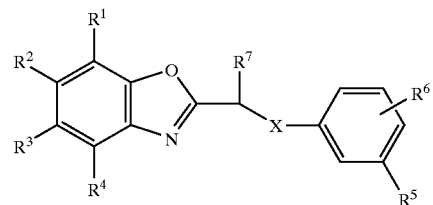

(1)

| Compound | R¹ | R² | R³ | R⁴ | R⁵ | R⁶ | R⁷ | X | Physical property |
|---|---|---|---|---|---|---|---|---|---|
| 492 | H | CH₃ | CH₃SO₂ | H | CN | H | C₃H₇-n | O | See Table 3 |
| 493 | H | Cl | F | H | CF₃ | 4-F | C₂H₅ | O | See Table 3 |
| 494 | H | Cl | F | H | CF₃ | 4-F | C₃H₇-n | O | See Table 3 |
| 495 | H | Cl | F | H | CF₃ | H | CH₃ | O | |
| 496 | H | Cl | F | H | CF₃ | H | C₂H₅ | O | See Table 3 |
| 497 | H | Cl | F | H | CF₃ | H | C₃H₇-n | O | See Table 3 |
| 498 | H | Cl | F | H | CN | H | C₂H₅ | O | See Table 3 |
| 499 | H | Cl | F | H | CN | 4-F | C₂H₅ | O | |
| 500 | H | Cl | F | H | CN | H | CH₃ | O | |
| 501 | H | Cl | F | H | CN | H | C₃H₇-n | O | See Table 3 |
| 502 | H | Cl | F | H | CN | 4-F | C₃H₇-n | O | |
| 503 | H | H | CH₃O | H | CF₃ | 4-F | C₂H₅ | O | See Table 3 |
| 504 | H | H | CH₃O | H | CF₃ | H | C₂H₅ | O | |
| 505 | H | H | CONH₂ | H | CF₃ | 4-F | C₂H₅ | O | |
| 506 | H | H | CONH₂ | H | CF₃ | H | C₂H₅ | O | |
| 507 | H | H | CH₃SO₂ | H | CN | H | C₂H₅ | O | |
| 508 | H | H | CH₃SO₂ | H | CN | H | C₃H₇-n | O | See Table 3 |
| 509 | H | H | CH₃SO₂ | H | CN | 4-Cl | C₂H₅ | O | See Table 3 |
| 510 | H | H | CH₃SO₂ | H | CN | 4-F | C₂H₅ | O | |
| 511 | H | H | CH₃SO₂ | H | CN | 4-Cl | C₃H₇-n | O | See Table 3 |
| 512 | H | H | CH₃SO₂ | H | CN | 4-F | C₃H₇-n | O | |
| 513 | H | H | CH₃SO₂ | H | CH₃SO₂ | H | C₂H₅ | O | See Table 3 |
| 514 | H | H | CH₃SO₂ | H | CH₃SO₂ | 4-Cl | C₂H₅ | O | |
| 515 | H | H | CH₃SO₂ | H | CH₃SO₂ | 4-F | C₂H₅ | O | |
| 516 | H | H | CH₃SO₂ | H | CH₃SO₂ | H | C₃H₇-n | O | See Table 3 |
| 517 | H | Cl | CN | H | CF₃ | 4-F | C₂H₅ | O | See Table 3 |
| 518 | H | H | CF₃CONH | H | CF₃ | 4-F | C₂H₅ | O | |
| 519 | H | H | CF₃CONH | H | CF₃ | H | C₂H₅ | O | |
| 520 | H | H | p-TolSO₂NH | H | CF₃ | 4-F | C₂H₅ | O | See Table 3 |
| 521 | H | H | p-TolSO₂NH | H | CF₃ | H | C₂H₅ | O | |
| 522 | H | H | CH₃SO₂NH | H | CF₃ | 4-F | C₂H₅ | O | See Table 3 |
| 523 | H | H | CH₃SO₂NH | H | CF₃ | H | C₂H₅ | O | |
| 524 | H | Cl | H | Cl | CF₃ | 4-F | C₂H₅ | O | See Table 3 |
| 525 | H | Cl | H | Cl | CF₃ | H | C₂H₅ | O | |
| 526 | H | Cl | H | Cl | CF₃ | H | C₃H₇-n | O | |
| 527 | H | CN | CN | H | OCF₃ | H | C₂H₅ | O | See Table 3 |
| 528 | H | CN | CN | H | OCF₃ | H | C₃H₇-n | O | |
| 529 | H | Cl | CN | H | CF₃ | H | C₂H₅ | O | See Table 3 |
| 530 | H | F | CN | H | CF₃ | Cl | C₂H₅ | O | See Table 3 |
| 531 | H | F | CN | H | CF₃ | Cl | C₃H₇-n | O | |
| 532 | H | Cl | CN | H | CF₃ | H | C₃H₇-n | O | See Table 3 |

TABLE 1-continued

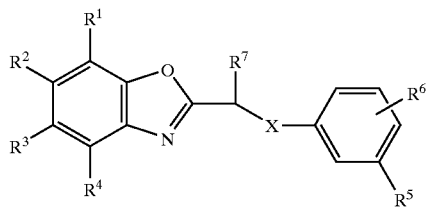

(1)

| Compound | R¹ | R² | R³ | R⁴ | R⁵ | R⁶ | R⁷ | X | Physical property |
|---|---|---|---|---|---|---|---|---|---|
| 533 | H | Cl | CN | H | $CF_3$ | 4-F | $C_3H_7$-n | O | See Table 3 |
| 534 | H | Cl | CN | H | $CF_3$ | 4-Cl | $C_2H_5$ | O | |
| 535 | H | Cl | CN | H | $CF_3$ | 4-Cl | $C_3H_7$-n | O | |
| 536 | H | Cl | CN | H | $CF_3$ | H | $CH_3$ | O | |

Incidentally, "m.p." means a melting point, and the unit thereof is "° C.", hereinafter the same.
Incidentally, "Tol" means toluene.

TABLE 2

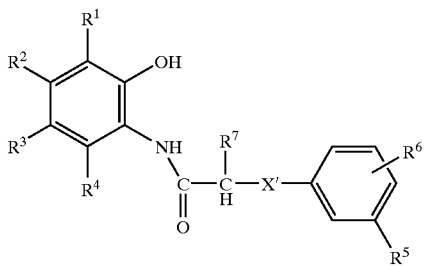

(6)

| Compound | R¹ | R² | R³ | R⁴ | R⁵ | R⁶ | R⁷ | X' | Physical property |
|---|---|---|---|---|---|---|---|---|---|
| 6-1 | H | H | H | H | $CF_3$ | 4-F | $C_2H_5$ | O | m.p. 123–124° C. |
| 6-2 | H | $CH_3$ | H | H | $CF_3$ | 4-F | $C_2H_5$ | O | m.p. 122–123° C. |
| 6-3 | H | $NO_2$ | Cl | H | $CF_3$ | 4-F | $C_2H_5$ | O | m.p. 181–183° C. |
| 6-4 | H | H | $CF_3$ | H | $CF_3$ | H | $C_3H_7$-n | O | m.p. 132–133° C. |

TABLE 3

| Compound | ¹H-NMR (300 MHz), $CDCl_3$, δ (ppm) |
|---|---|
| 9 | 7.04–7.65 (6H, m), 5.28 (1H, t), 2.17–2.32 (2H, m), 1.10 (3H, t) |
| 10 | 7.15–7.65 (7H, m), 5.37 (1H, t), 2.18–2.32 (2H, m), 1.01 (3H, t) |
| 27 | 7.05–7.68 (6H, m), 5.23 (1H, dd), 2.19–2.32 (2H, m), 1.10 (3H, t) |
| 39 | 7.06–8.46 (6H, m), 5.36 (1H, dd), 2.21–2.35 (2H, m), 1.13 (3H, t) |
| 51 | 7.03–7.36 (6H, m), 5.31 (1H, t), 2.61 (3H, t), 2.17–2.33 (2H, m), 1.10 (3H, t) |
| 57 | 7.06–8.24 (6H, m), 5.48 (1H, dd), 2.20–2.36 (2H, m), 1.14 (3H, t) |
| 63 | 6.57–7.31 (6H, m), 5.25 (1H, t), 2.16–2.31 (2H, m), 1.09 (3H, t) |
| 69 | 7.09–8.31 (7H, m), 5.27 (1H, t), 2.28 (3H, t), 2.18–2.32 (2H, m), 1.10 (3H, t) |

TABLE 3-continued

| Compound | ¹H-NMR (300 MHz), $CDCl_3$, δ (ppm) |
|---|---|
| 75 | 7.07–7.92 (5H, m), 5.35 (1H, t), 2.18–2.36 (2H, m), 1.13 (3H, t) |
| 76 | 7.06–7.92 (6H, m), 5.43 (1H, dd), 2.23–2.37 (2H, m), 1.14 (3H, t) |
| 81 | 7.06–7.92 (6H, m), 5.43 (1H, dd), 2.23–2.37 (2H, m), 1.14 (3H, t) |
| 86 | 7.16–7.85 (7H, m), 5.42 (1H, t), 2.22–2.35 (2H, m), 1.12 (3H, t) |
| 93 | 7.05–7.85 (6H, m), 5.34 (1H, t), 2.20–2.34 (2H, m), 1.14 (3H, t) |
| 94 | 7.16–7.85 (7H, m), 5.42 (1H, t), 2.22–2.35 (2H, m), 1.12 (3H, t) |
| 101 | 7.04–7.85 (6H, m), 5.41 (1H, dd), 2.11–2.29 (2H, m), 1.48–1.62 (2H, m), 1.02 (3H, t) |
| 119 | 7.06–7.48 (6H, m), 5.37 (1H, t), 2.18–2.33 (2H, m), 1.11 (3H, t) |
| 120 | 7.04–7.48 (6H, m), 5.28 (1H, t), 2.17–2.31 (2H, m), 1.10 (3H, t) |
| 137 | 6.99–7.72 (6H, m), 5.53 (1H, t), 1.87 (3H, d) |
| 138 | 6.96–7.72 (6H, m), 5.61 (1H, dd), 1.87 (3H, d) |
| 139 | 7.04–7.71 (6H, m), 5.29 (1H, t), 2.17–2.32 (2H, m), 1.10 (3H, t) |
| 140 | 7.16–7.72 (7H, m), 5.37 (1H, t), 2.18–2.33 (2H, m), 1.10 (3H, t) |
| 141 | 7.03–7.71 (6H, m), 5.36 (1H, dd), 2.08–2.27 (2H, m), 1.49–1.59 (2H, m), 1.01 (3H, t) |
| 142 | 7.16–7.71 (7H, m), 5.44 (1H, dd), 2.10–2.27 (2H, m), 1.48–1.59 (2H, m), 1.01 (3H, t) |
| 154 | 7.29–7.63 (7H, m), 4.33 (1H, dd), 2.10–2.26 (2H, m), 1.10 (3H, t) |
| 160 | 7.22–7.91 (7H, m), 4.51 (1H, dd), 2.26–2.48 (2H, m), 1.02 (3H, t) |
| 165 | 7.04–7.87 (6H, m), 5.28 (1H, t), 2.17–2.32 (2H, m), 1.10 (3H, t) |
| 166 | 7.15–7.87 (7H, m), 5.37 (1H, t), 2.20–2.32 (2H, m), 1.10 (3H, t) |
| 171 | 7.04–8.07 (6H, m), 5.28 (1H, t), 2.16–2.31 (2H, m), 1.09 (3H, t) |
| 172 | 7.15–8.07 (7H, m), 5.37 (1H, t), 2.17–2.32 (2H, m), 1.10 (3H, t) |
| 176 | 7.00–8.65 (7H, m), 5.68 (1H, dd), 1.91 (3H, d) |
| 177 | 7.06–8.62 (7H, m), 5.35 (1H, dd), 2.10–2.35 (2H, m), 1.25 (3H, t) |
| 178 | 7.17–8.64 (7H, m), 5.44 (1H, t), 2.15–2.36 (2H, m), 1.13 (3H, t) |

TABLE 3-continued

| Compound | $^1$H-NMR (300 MHz), CDCl$_3$, δ (ppm) |
|---|---|
| 183 | 7.02–7.51 (6H, m), 5.28 (1H, t), 2.17–2.31 (2H, m), 1.09 (3H, t) |
| 189 | 7.06–8.07 (6H, m), 5.34 (1H, dd), 2.19–2.33 (2H, m), 1.11 (3H, t) |
| 190 | 7.16–8.07 (7H, m), 5.42 (1H, t), 2.20–2.35 (2H, m), 0.88 (3H, t) |
| 191 | 7.05–8.06 (6H, m), 5.40 (1H, dd), 2.10–2.28 (2H, m), 1.48–1.59 (2H, m), 1.01 (3H, t) |
| 192 | 7.19–8.03 (7H, m), 5.51 (1H, dd), 2.11–2.36 (2H, m), 1.47–1.67 (2H, m), 1.02 (3H, t) |
| 193 | 7.03–8.07 (6H, m), 5.08 (1H, dd), 2.10–2.28 (2H, m), 1.48–1.59 (2H, m), 1.01 (3H, t) |
| 197 | 7.05–8.02 (6H, m), 5.34 (1H, dd), 2.19–2.34 (2H, m), 1.10 (3H, t) |
| 198 | 7.17–8.02 (7H, m), 5.42 (1H, t), 2.21–2.35 (2H, m), 1.12 (3H, t) |
| 199 | 7.04–8.02 (6H, m), 5.41 (1H, dd), 2.10–2.29 (2H, m), 1.48–1.62 (2H, m), 1.02 (3H, t) |
| 200 | 7.18–8.07 (7H, m), 5.52 (1H, dd), 2.13–2.31 (2H, m), 1.51–1.64 (2H, m), 1.02 (3H, t) |
| 215 | 7.05–8.36 (6H, m), 5.36 (1H, t), 3.10 (3H, s), 2.21–2.34 (2H, m), 1.12 (3H, t) |
| 216 | 7.18–8.36 (7H, m), 5.44 (1H, t), 3.09 (3H, s), 2.20–2.37 (2H, m), 1.12 (3H, t) |
| 217 | 7.05–8.35 (6H, m), 5.42 (1H, dd), 3.09 (3H, s), 2.11–2.29 (2H, m), 1.48–1.63 (2H, m), 1.02 (3H, t) |
| 218 | 7.05–8.35 (6H, m), 5.51 (1H, dd), 3.09 (3H, s), 2.12–2.31 (2H, m), 1.50–1.55 (2H, m), 1.02 (3H, t) |
| 221 | 7.06–8.32 (6H, m), 5.36 (1H, t), 3.16 (2H, q), 2.21–2.34 (2H, m), 1.29 (3H, t), 1.12 (3H, t) |
| 227 | 7.05–7.61 (6H, m), 5.31 (1H, t), 2.18–2.32 (2H, m), 1.10 (3H, t) |
| 228 | 7.17–7.61 (7H, m), 5.39 (1H, t), 2.19–2.34 (2H, m), 1.11 (3H, t) |
| 233 | 7.05–8.44 (6H, m), 5.32 (1H, t), 4.41 (2H, q), 2.19–2.34 (2H, m), 1.41 (3H, t), 1.11 (3H, t) |
| 234 | 7.18–8.44 (7H, m), 5.41 (1H, t), 4.41 (2H, q), 2.20–2.35 (2H, m), 1.41 (3H, t), 1.12 (3H, t) |
| 240 | 7.19–8.54 (7H, m), 5.45 (1H, t), 2.21–2.34 (2H, m), 1.13 (3H, t) |
| 245 | 6.99–7.91 (6H, m), 5.28 (1H, t), 2.14–2.31 (2H, m), 2.20 (3H, m), 1.09 (3H, t) |
| 252 | 7.22–7.97 (7H, m), 4.35 (1H, dd), 2.12–2.26 (2H, m), 1.21 (3H, t) |
| 258 | 7.35–7.93 (7H, m), 4.37 (1H, dd), 2.12–2.28 (2H, m), 1.11 (3H, t) |
| 264 | 7.63–8.00 (7H, m), 4.55 (1H, dd), 2.31–2.48 (2H, m), 1.03 (3H, t) |
| 270 | 7.61–7.95 (7H, m), 4.55 (1H, dd), 2.31–2.54 (2H, m), 1.03 (3H, t) |
| 283 | 7.15–7.55 (6H, m), 5.36 (1H, t), 2.16–2.34 (2H, m), 1.01 (3H, t) |
| 284 | 7.43–8.12 (5H, m), 5.83 (1H, t), 2.12–2.18 (2H, m), 1.01 (3H, t) |
| 285 | 7.16–7.55 (5H, m), 5.43 (1H, dd), 2.09–2.27 (2H, m), 1.47–1.62 (2H, m), 1.01 (3H, t) |
| 286 | 7.03–7.55 (5H, m), 5.34 (1H, dd), 2.07–2.26 (2H, m), 1.45–1.60 (2H, m), 1.01 (3H, t) |
| 291 | 7.15–7.78 (6H, m), 5.36 (1H, t), 2.06–2.29 (2H, m), 1.10 (3H, t) |
| 292 | 7.04–7.78 (5H, m), 5.28 (1H, dd), 2.20–2.28 (2H, m), 1.09 (3H, t) |
| 293 | 7.15–7.77 (6H, m), 5.43 (1H, dd), 2.09–2.27 (2H, m), 1.50–1.55 (2H, m), 1.01 (3H, t) |
| 294 | 7.04–7.76 (5H, m), 5.34 (1H, dd), 2.07–2.28 (2H, m), 1.49–1.57 (2H, m), 1.01 (3H, t) |
| 298 | 7.04–7.82 (5H, m), 5.28 (1H, t), 2.17–2.30 (2H, m), 1.10 (3H, t) |
| 300 | 7.03–7.82 (5H, m), 5.35 (1H, dd), 2.08–2.32 (2H, m), 1.46–1.61 (2H, m), 1.01 (3H, t) |
| 315 | 7.05–8.19 (6H, m), 5.47 (1H, t), 2.22–2.35 (2H, m), 1.13 (3H, t) |
| 317 | 7.13–8.18 (6H, m), 5.53 (1H, dd), 2.04–2.30 (2H, m), 1.51–1.63 (2H, m), 1.02 (3H, t) |
| 334 | 7.07–8.10 (5H, m), 5.35 (1H, dd), 2.20–2.34 (2H, m), 1.12 (3H, t) |
| 339 | 7.15–7.71 (6H, m), 5.36 (1H, t), 2.46 (3H, s), 2.16–2.34 (2H, m), 1.09 (3H, t) |
| 342 | 7.02–7.70 (5H, m), 5.33 (1H, dd), 2.47 (3H, s), 2.07–2.25 (2H, m), 1.45–1.60 (2H, m), 1.00 (3H, t) |
| 345 | 7.15–8.01 (5H, m), 5.40 (1H, t), 2.17–2.35 (2H, m), 1.12 (3H, t) |
| 346 | 7.06–8.01 (5H, m), 5.32 (1H, t), 2.18–2.31 (2H, m), 1.11 (3H, t) |
| 347 | 7.15–8.00 (5H, m), 5.46 (1H, dd), 2.10–2.28 (2H, m), 1.51–1.62 (2H, m), 1.01 (3H, t) |
| 348 | 7.05–8.01 (5H, m), 5.38 (1H, dd), 2.05–2.27 (2H, m), 1.43–1.16 (2H, m), 1.01 (3H, t) |
| 353 | 7.23–7.72 (7H, m), 5.34 (1H, dd), 2.18–2.32 (2H, m), 1.10 (3H, t) |
| 362 | 7.28–7.71 (7H, m), 5.42 (1H, t), 3.00 (3H, t), 2.23–2.31 (2H, m), 1.11 (3H, t) |
| 363 | 7.25–7.70 (7H, m), 5.48 (1H, t), 3.00 (3H, t), 2.16–2.23 (2H, m), 1.40–1.60 (2H, m), 1.00 (3H, t) |
| 368 | 7.32–7.73 (6H, m), 5.42 (1H, t), 2.24–2.37 (2H, m), 1.11 (3H, t) |
| 369 | 7.31–7.72 (6H, m), 5.48 (1H, dd), 2.17–2.31 (2H, m), 1.50–1.70 (2H, m), 1.01 (3H, t) |
| 373 | 7.21–7.72 (7H, m), 5.09 (1H, d), 2.54 (1H, dq), 1.18 (3H, d), 1.01 (3H, d) |
| 377 | 7.29–7.73 (6H, m), 5.16 (1H, d), 2.60 (1H, dq), 1.19 (3H, d), 1.03 (3H, d) |
| 381 | 7.23–7.71 (7H, m), 5.17 (1H, d), 3.03 (3H, s), 2.57 (1H, dq), 1.19 (3H, d), 1.03 (3H, d) |
| 383 | 7.25–8.03 (7H, m), 5.39 (1H,t), 2.21–2.34 (2H, m), 1.11 (3H, t) |
| 384 | 7.24–8.03 (7H, m), 5.49 (1H, dd), 2.13–2.31 (2H, m), 1.50–1.64 (2H, m), 1.02 (3H, t) |
| 385 | 7.23–8.03 (7H, m), 5.13 (1H, d), 2.57 (1H, dq), 1.20 (3H, d), 1.02 (3H, d) |
| 386 | 7.21–8.08 (12H, m), 6.51 (1H, s), 2.10–2.28 (2H, m) |
| 388 | 7.22–8.04 (6H, m), 5.47 (1H, t), 2.05–2.41 (2H, m), 1.12 (3H, t) |
| 389 | 7.34–8.03 (6H, m), 5.44 (1H, dd), 2.04–2.34 (2H, m), 1.48–1.60 (2H, m), 1.03 (3H, t) |
| 390 | 7.30–8.04 (6H, m), 5.12 (1H, d), 2.62 (1H, dq), 1.20 (3H, d), 1.04 (3H, d) |
| 392 | 7.25–8.08 (7H, m), 5.39 (1H, t), 2.13–2.34 (2H, m), 1.16 (3H, t) |
| 393 | 7.24–8.07 (7H, m), 5.46 (1H, t), 2.14–2.29 (2H, m), 1.51–1.58 (2H, m), 1.01 (3H, t) |
| 396 | 6.82–8.07 (7H, m), 5.37 (1H, t), 2.19–2.32 (2H, m), 1.11 (3H, t) |
| 400 | 7.32–8.08 (6H, m), 5.53 (1H, dd), 2.19–2.33 (2H, m), 1.51–1.61 (2H, m), 1.02 (3H, t) |
| 401 | 7.26–8.08 (6H, m), 5.22 (1H, d), 2.62 (1H, dq), 1.19 (3H, d), 1.04 (3H, d) |
| 403 | 7.27–8.06 (7H, m), 5.49 (1H, t), 3.01 (3H, s), 2.25–2.33 (2H, m), 1.12 (3H, t) |
| 404 | 7.29–8.06 (7H, m), 5.53 (1H, dd), 3.01 (3H, s), 2.16–2.31 (2H, m), 1.52–1.58 (2H, m), 1.02 (3H, t) |
| 405 | 7.22–8.06 (7H, m), 5.22 (1H, d), 3.00 (3H, s), 2.58 (1H, dq), 1.20 (3H, d), 1.04 (3H, d) |
| 408 | 7.28–8.01 (7H, m), 5.53 (1H, dd), 3.00 (3H, s), 2.18–2.28 (2H, m), 1.52–1.58 (2H, m), 1.02 (3H, t) |
| 409 | 7.24–8.01 (7H, m), 5.21 (1H, d), 2.99 (3H, s), 2.59 (1H, dq), 1.20 (3H, d), 1.04 (3H, d) |
| 411 | 7.23–7.56 (6H, m), 5.32 (1H, t), 2.18–2.31 (2H, m), 1.10 (3H, t) |
| 412 | 7.24–7.56 (6H, m), 5.42 (1H, dd), 2.10–2.28 (2H, m), 1.47–1.62 (2H, m), 1.01 (3H, t) |
| 414 | 7.22–7.78 (6H, m), 5.33 (1H, t), 2.18–2.31 (2H, m), 1.10 (3H, t) |
| 415 | 7.22–7.78 (6H, m), 5.39 (1H, dd), 2.09–2.27 (2H, m), 1.49–1.58 (2H, m), 1.01 (3H, t) |
| 417 | 7.31–7.80 (5H, m), 5.41 (1H, t), 2.26–2.33 (2H, m), 1.10 (3H, t) |
| 418 | 7.31–7.79 (5H, m), 5.47 (1H, t), 2.17–2.30 (2H, m), 1.47–1.60 (2H,m), 1.02 (3H, t) |
| 420 | 7.26–7.77 (6H, m), 5.41 (1H, t), 3.00 (3H, s), 2.23–2.30 (2H, m), 1.10 (3H, t) |

TABLE 3-continued

| Compound | ¹H-NMR (300 MHz), CDCl₃, δ (ppm) |
|---|---|
| 421 | 7.25–7.77 (6H, m), 5.47 (1H, dd), 3.00 (3H, s), 2.15–2.25 (2H, m), 1.50–1.62 (2H, m), 1.01 (3H, t) |
| 423 | 7.23–8.02 (6H, m), 5.37 (1H, t), 2.22–2.32 (2H, m), 1.11 (3H, t) |
| 424 | 7.23–8.01 (6H, m), 5.43 (1H, dd), 2.14–2.25 (2H, m), 1.49–1.58 (2H, m), 1.02 (3H, t) |
| 426 | 7.06–7.72 (7H, m), 5.39 (1H, t), 2.18–2.32 (2H, m), 1.10 (3H, t) |
| 432 | 7.10–8.64 (6H, m), 5.41 (1H, t), 2.23–2.38 (2H, m), 1.13 (3H, t) |
| 435 | 6.95–8.64 (7H, m), 5.41 (1H, t), 2.17–2.35 (2H, m), 1.12 (3H, t) |
| 438 | 7.08–7.72 (6H, m), 5.33 (1H, t), 2.14–2.36 (2H, m), 1.10 (3H, t) |
| 441 | 7.07–7.48 (6H, m), 5.33 (1H, t), 2.18–2.32 (2H, m), 1.10 (3H, t) |
| 444 | 7.10–7.61 (6H, m), 5.35 (1H, t), 2.19–2.33 (2H, m), 1.11 (3H, t) |
| 447 | 6.81–7.72 (7H, m), 5.33 (1H, t), 2.15–2.33 (2H, m), 1.09 (3H, t) |
| 450 | 6.82–8.63 (7H, m), 5.40 (1H, t), 2.09–2.36 (2H, m), 1.12 (3H, t) |
| 453 | 6.92–8.01 (7H, m), 5.34 (1H, t), 2.17–2.33 (2H, m), 1.10 (3H, t) |
| 457 | 7.24–7.71 (7H, m), 5.41 (1H, dd), 2.10–2.28 (2H, m), 1.47–1.64 (2H, m), 1.01 (3H, t) |
| 459 | 7.32–7.71 (5H, m), 5.41 (1H, t), 2.24–2.38 (2H, m), 1.10 (3H, t) |
| 460 | 7.28–7.72 (5H, m), 5.51 (1H, dd), 2.15–2.31 (2H, m), 1.47–1.60 (2H, m), 1.02 (3H, t) |
| 462 | 7.25–7.61 (6H, m), 5.41 (1H, t), 2.20–2.33 (2H, m), 1.11 (3H, t) |
| 463 | 7.25–7.60 (6H, m), 5.47 (1H, dd), 3.01 (3H, s), 2.16–2.25 (2H, m), 1.47–1.60 (2H, m), 1.02 (3H, t) |
| 465 | 7.31–8.03 (5H, m), 5.45 (1H, t), 2.27–2.34 (2H, m), 1.12 (3H, t) |
| 466 | 7.31–8.03 (5H, m), 5.52 (1H, t), 2.18–2.29 (2H, m), 1.50–1.57 (2H, m), 1.02 (3H, t) |
| 468 | 7.25–8.01 (6H, m), 5.45 (1H, dd), 3.02 (3H, s), 2.22–2.34 (2H, m), 1.12 (3H, t) |
| 469 | 7.25–8.00 (6H, m), 5.51 (1H, dd), 3.02 (3H, s), 2.12–2.27 (2H, m), 1.49–1.62 (2H, m), 1.02 (3H, t) |
| 471 | 7.05–7.81 (5H, m), 5.33 (1H, t), 2.19–2.34 (2H, m), 1.11 (3H, t) |
| 474 | 7.04–7.81 (5H, m), 5.39 (1H, dd), 2.09–2.32 (2H, m), 1.48–1.62 (2H, m), 1.01 (3H, t) |
| 476 | 7.03–7.71 (6H, m), 5.34 (1H, dd), 2.11–2.24 (2H, m), 1.40–1.54 (4H, m), 0.93 (3H, t) |
| 479 | 7.23–7.72 (7H, m), 5.39 (1H, dd), 2.17–2.35 (2H, m), 1.40–1.57 (4H, m), 0.93 (3H, t) |
| 481 | 7.23–7.71 (6H, m), 5.32 (1H, t), 2.48 (3H, s), 2.18–2.31 (2H, m), 1.09 (3H, t) |
| 484 | 7.23–7.71 (6H, m), 5.38 (1H, dd), 2.48 (3H, s), 2.11–2.32 (2H, m), 1.49–1.55 (2H, m), 1.00 (3H, t) |
| 487 | 7.04–8.48 (5H, m), 5.33 (1H, t), 3.11 (3H, s), 2.83 (3H, s), 2.21–2.30 (2H, m), 1.10 (3H, t) |
| 489 | 7.17–8.48 (6H, m), 5.48 (1H, dd), 3.11 (3H, s), 2.83 (3H, s), 2.12–2.29 (2H, m), 1.40–1.60 (2H, m), 1.01 (3H, t) |
| 490 | 7.17–8.48 (6H, m), 5.41 (1H, t), 3.11 (3H, s), 2.83 (3H, s), 2.20–2.33 (2H, m), 1.10 (3H, t) |
| 491 | 7.25–8.48 (6H, m), 5.38 (1H, t), 3.11 (3H, s), 2.83 (3H, s), 2.20–2.35 (2H, m,), 1.11 (3H, t) |
| 492 | 7.25–8.48 (6H, m), 5.45 (1H, dd), 3.11 (3H, s), 2.83 (3H, s), 2.10–2.29 (2H, m), 1.40–1.60 (2H, m), 1.01 (3H, t) |
| 493 | 7.04–7.61 (5H, m), 5.28 (1H, t), 2.15–2.33 (2H, m), 1.09 (3H, t) |
| 494 | 7.04–7.61 (5H, m), 5.34 (1H, dd), 2.10–2.26 (2H, m), 1.49–1.60 (2H, m), 1.01 (3H, t) |
| 496 | 7.18–7.61 (6H, m), 5.37 (1H, m), 2.21–2.29 (2H, m), 1.10 (3H, t) |
| 497 | 7.14–7.60 (6H, m), 5.43 (1H, m), 2.09–2.27 (2H, m), 1.47–1.61 (2H,m), 1.01 (3H, t) |
| 498 | 7.23–7.61 (6H, m), 5.33 (1H, t), 2.18–2.31 (2H, m), 1.10 (3H, t) |
| 501 | 7.22–7.61 (6H, m), 5.40 (1H, dd), 2.09–2.27 (2H, m), 1.46–1.61 (2H, m), 1.01 (3H, t) |
| 503 | 6.94–7.42 (6H, m), 5.26 (1H, t), 3.85 (3H, s), 2.18–2.30 (2H, m), 1.09 (3H, t) |
| 508 | 7.26–8.36 (7H, m), 5.47 (1H, dd), 3.10 (3H, s), 2.15–2.30 (2H, m), 1.46–1.61 (2H, m), 1.02 (3H, t) |
| 509 | 7.22–8.36 (6H, m), 5.43 (1H, t), 3.10 (3H, s), 2.30–2.44 (2H, m), 1.16 (3H, t) |
| 511 | 7.22–8.36 (6H, m), 5.50 (1H, dd), 3.10 (3H, s), 2.22–2.37 (2H, m), 1.40–1.60 (2H, m), 1.03 (3H, t) |
| 513 | 7.27–8.35 (7H, m), 5.49 (1H, t), 3.09 (3H, s), 3.05 (3H, s), 2.24–2.36 (2H, m), 1.13 (3H, t) |
| 516 | 7.27–8.35 (6H, m), 5.55 (1H, dd), 3.09 (3H, s), 3.04 (3H, s), 2.17–2.32 (2H, m), 1.53–1.64 (2H, m), 1.02 (3H, t) |
| 517 | 7.05–8.06 (5H, m), 5.32 (1H, t), 2.16–2.34 (2H, m), 1.11 (3H, t) |
| 520 | 6.93–7.66 (10H, m), 5.26 (1H, t), 2.37 (3H, s), 2.15–2.30 (2H, m), 1.08 (3H, t) |
| 522 | 6.80–7.65 (7H, m), 5.30 (1H, t), 3.01 (3H, s), 2.18–2.28 (2H, m), 1.08 (3H, t) |
| 524 | 7.03–7.48 (5H, m), 5.33 (1H, t), 2.16–2.29 (2H, m), 1.10 (3H, t) |
| 527 | 6.85–8.19 (6H, m), 5.42 (1H, dd), 2.20–2.36 (2H, m), 1.12 (3H, t) |
| 529 | 7.14–8.06 (6H, m), 5.41 (1H, t), 2.04–2.35 (2H, m), 1.12 (3H, t) |
| 530 | 7.07–8.01 (5H, m), 5.36 (1H, t), 2.04–2.34 (2H, m), 1.11 (3H, t) |
| 532 | 7.14–8.05 (6H, m), 5.47 (1H, dd), 2.12–2.28 (2H, m), 1.49–1.62 (2H, m), 1.02 (3H, t) |
| 533 | 7.05–8.05 (5H, m), 5.39 (1H, dd), 2.09–2.32 (2H, m), 1.48–1.61 (2H, m), 1.02 (3H, t) |

Example 2

Preparation of Preparations (1) Preparation of Granule 5 parts by weight of Compound 1 was uniformly mixed with 35 parts by weight of bentonite, 57 parts by weight of talc, 1 part by weight of sodium decylbenzensulfonate and 2 parts by weight of sodium lignosulfonate, and then, the mixture was kneaded with addition of a small amount of water, followed by subjected to granulation and drying, to obtain a granule.

(2) Preparation of Wettable Powder 10 parts by weight of Compound 1 was uniformly mixed with 70 parts by weight of kaolin clay, 18 parts by weight of white carbon, 1.5 parts by weight of sodium dodecylbenzenesulfonate and 0.5 part by weight of sodium β-naphthalene sulfonate-formalin condensate, and then, the mixture was pulverized by air mill to obtain a wettable powder.

(3) Preparation of Emulsion

To the mixture of 20 parts by weight of Compound 1 and 70 parts by weight of xylene was added 10 parts by weight of Sorpol 3005X (trade name,. produced by Toho Kagaku Kogyo), and the mixture was uniformly mixed and dissolved to obtain an emulsion.

(4) Preparation of dust 5 parts by weight of Compound 1, 50 parts by weight of talc and 45 parts by weight of kaolin clay were uniformly mixed to obtain a dust.

Example 3

Herbicidal Activity Test (1) Herbicidal Test for Paddy Field

Wagner pots, each having an area of 1/5000 are, were packed with Ube soil (alluvial soil) and planted with seeds or tubers of young rice plant, barnyardgrass, bulrush, flat sedge and monochoria. Then, the pots were filled with water to a depth of 3 cm.

Each wettable powder of the desired compounds (I) shown in Table 1 prepared in accordance with Example 2 was diluted with water containing a surfactant (0.05%) and subjected to dropwise addition treatment by using pipet so that an effective concentration of the compound (I) in each herbicide became 500 g/ha at 1.5 leaf stage of barnyardgrass.

These plants were controlled in a glass house at an average temperature of 25° C. for 3 weeks, and then herbicidal effects thereof were investigated.

The herbicidal effects are evaluated according to the following 6 ranks as compared with non-treated district.
(0: normal development, 1: Less damaged, 2: Slightly damaged, 3: Moderately damaged, 4: Severely damaged, 5: All killed).

As a result, all compounds (1) showed bleaching effect. The degrees of these effects are shown in Table 4. Incidentally, "-" in the column means not investigated.

TABLE 4

| Compound | Young rice plant | Barnyardgrass | Bulrush | Flat sedge | Monochoria |
|---|---|---|---|---|---|
| 9 | 0 | 3 | 3 | — | 4 |
| 10 | 0 | 4 | 3 | — | 1 |
| 27 | 0 | 1 | 4 | — | 5 |
| 119 | 1 | 3 | — | 2 | 4 |
| 120 | 1 | 4 | 3 | 2 | 5 |
| 137 | 1 | 3 | 3 | — | 3 |
| 138 | 0 | 2 | 2 | 3 | 3 |
| 139 | 2 | 5 | 5 | — | 5 |
| 140 | 1 | 5 | — | — | 5 |
| 141 | 1 | 5 | 5 | — | 5 |
| 142 | 1 | 3 | 3 | — | 5 |
| 165 | 2 | 4 | — | 3 | 5 |
| 166 | 1 | 3 | — | 4 | 5 |
| 177 | 2 | 5 | 5 | 3 | 5 |
| 189 | 2 | 5 | 5 | 5 | 5 |
| 190 | 3 | 5 | — | 3 | 5 |
| 192 | 1 | 5 | 4 | 4 | 5 |
| 197 | 3 | 4 | — | — | 5 |
| 198 | 1 | 4 | 1 | — | 5 |
| 199 | 1 | 4 | 5 | — | 5 |
| 200 | 0 | 2 | 2 | — | 5 |
| 217 | 1 | — | 2 | — | 4 |
| 284 | 2 | 4 | 4 | 4 | 5 |
| 286 | 3 | 4 | 5 | 3 | 5 |
| 315 | 1 | 3 | 2 | — | 4 |
| 316 | 0 | — | 3 | — | 5 |
| 317 | 1 | 3 | 3 | 5 | 5 |
| 339 | 1 | 4 | 4 | — | 5 |
| 340 | 0 | 5 | 4 | 2 | 5 |
| 346 | 2 | 5 | 5 | 5 | 5 |
| 348 | 2 | 4 | 4 | 4 | 5 |
| 353 | 0 | 3 | 4 | — | 5 |
| 392 | 0 | 5 | 5 | 5 | 5 |
| 393 | 0 | 4 | 5 | 5 | 5 |
| 396 | 2 | 2 | 5 | 5 | 5 |
| 441 | 1 | 5 | — | 2 | 5 |
| 450 | 1 | 4 | 4 | 3 | 5 |
| 457 | 1 | 4 | 4 | 4 | 4 |
| 471 | — | 5 | 2 | 5 | 5 |
| 474 | — | 2 | — | — | 5 |
| 491 | 0 | — | 3 | — | 5 |
| 492 | 0 | 2 | 3 | — | 5 |
| 493 | — | 5 | — | — | 5 |
| 494 | — | 5 | 3 | — | 5 |
| 497 | 2 | 4 | 2 | — | 4 |
| 498 | 1 | 3 | 3 | — | 2 |
| 501 | 1 | 3 | — | — | 3 |
| 517 | 2 | 3 | 3 | — | 3 |
| 527 | 2 | 4 | 3 | 3 | 4 |
| 529 | — | 5 | 5 | 4 | 5 |
| 530 | — | 5 | 5 | 5 | 5 |
| 532 | — | 5 | 5 | 2 | 5 |
| 533 | 2 | 5 | — | 2 | 4 |

(2) Soil Treatment Test for Upland Field

Wagner pots, each having an area of 1/5000 are, were packed with Ube soil (alluvial soil), and then each seed of corn, soybean, cotton, wheat, solgum, sugar beat, Large crabgrass, barnyardgrass, green foxtail, blackgrass, annual bluegrass, common lambsquartes, livid amaranth and velvetleaf were planted and covered with soil.

Each wettable powder of the desired compounds (I) shown in Table 1 prepared in accordance with Example 2 was diluted with water containing a surfactant (0.05%) and uniformly sprayed on the surface of each soil so that an effective concentration of the compound (I) in each herbicide became 500 g/ha. These plants were controlled in a glass house at an average temperature of 25° C. for 3 weeks, and then herbicidal effects thereof were investigated.

The herbicidal effects were evaluated according to the evaluation method described in the above (1).

As a result, all compounds (1) showed a bleaching effect. The degree of these effects is shown in Table 5.

TABLE 5

| Compound | Corn | Soybean | Cotton | Wheat | Solgum | Sugar beat | Large crabgrass | Barnyardgrass | Green foxtail | Blackgrass | Annual bluegrass | Common lambsquarters | Livid amaranth | Velvetleaf |
|---|---|---|---|---|---|---|---|---|---|---|---|---|---|---|
| 9 | 0 | 0 | 0 | 0 | 0 | 2 | 5 | 4 | 5 | 3 | 4 | 3 | 5 | — |
| 10 | 0 | 0 | 0 | 0 | 0 | 0 | 5 | 2 | 4 | 2 | 4 | 2 | 4 | — |
| 27 | 0 | 0 | 0 | 0 | 0 | 1 | 4 | 1 | 4 | — | 3 | 3 | 5 | 1 |
| 39 | 0 | 0 | 1 | 0 | 0 | 2 | 4 | — | 4 | — | 4 | 3 | 5 | — |

TABLE 5-continued

| | Effects | | | | | | | | | | | | |
|---|---|---|---|---|---|---|---|---|---|---|---|---|---|
| Compound | Corn | Soybean | Cotton | Wheat | Solgum | Sugar beat | Large crabgrass | Barnyardgrass | Green foxtail | Blackgrass | Annual bluegrass | Common lambsquarters | Livid amaranth | Velvetleaf |
| 86 | 0 | 0 | — | 0 | 0 | 2 | 5 | 3 | 4 | — | 1 | 1 | 5 | — |
| 93 | 1 | 2 | 1 | 0 | 1 | 5 | 5 | 4 | 5 | 3 | 5 | 3 | 5 | 2 |
| 94 | 0 | 0 | — | 0 | 0 | 2 | 5 | 3 | 4 | — | 1 | 1 | 5 | 0 |
| 101 | 0 | 0 | 0 | 0 | 1 | 2 | 5 | 3 | 5 | 3 | 5 | 4 | 5 | 2 |
| 119 | 0 | 0 | 0 | 0 | 0 | 5 | 5 | 5 | 5 | 3 | 5 | 1 | 5 | — |
| 120 | 0 | 0 | 0 | 0 | 1 | 3 | 5 | 4 | 5 | 3 | 5 | 4 | 3 | 3 |
| 137 | 1 | 0 | 0 | 1 | 1 | 2 | 5 | 3 | 5 | 3 | 5 | 2 | 5 | — |
| 138 | 0 | 0 | 0 | 0 | 0 | — | 4 | 1 | 2 | 5 | 3 | 3 | 5 | — |
| 139 | 2 | 1 | 1 | 1 | 2 | 5 | 5 | 3 | 5 | 5 | 5 | 4 | 5 | 5 |
| 140 | 0 | 0 | 0 | 0 | 1 | 3 | 5 | 4 | 5 | 4 | 5 | 4 | 5 | 1 |
| 141 | 1 | 2 | — | 0 | 2 | 5 | 5 | 3 | 5 | 5 | 5 | 5 | 5 | 5 |
| 142 | 1 | 3 | 0 | 1 | 1 | 5 | 5 | 3 | 5 | 5 | 5 | 5 | 5 | 5 |
| 165 | 2 | 0 | 0 | 0 | 1 | 5 | 5 | 5 | 5 | 4 | 5 | 3 | 5 | 1 |
| 166 | 0 | 0 | 0 | 0 | 0 | 5 | 5 | 4 | 5 | 3 | 5 | 2 | 5 | — |
| 171 | 0 | 0 | 0 | 1 | 1 | 5 | 5 | 2 | 5 | 1 | 5 | 2 | 5 | — |
| 172 | 0 | 0 | 0 | 0 | 0 | 0 | 5 | — | 5 | 1 | 3 | — | 5 | — |
| 177 | 2 | 1 | 2 | 2 | 2 | 5 | 5 | 3 | 5 | 5 | 5 | 4 | 5 | 5 |
| 178 | 0 | 0 | 0 | 0 | 0 | 1 | 5 | 4 | 5 | 3 | 5 | 4 | 5 | 1 |
| 190 | 2 | 0 | 5 | 2 | 2 | 5 | 5 | 5 | 5 | 3 | 5 | 4 | 5 | 3 |
| 192 | 2 | 0 | 1 | 2 | 2 | 5 | 5 | 3 | 5 | 5 | 5 | 5 | 5 | 5 |
| 197 | 2 | — | 3 | 2 | 2 | 5 | 5 | 5 | 5 | 5 | 5 | 4 | 5 | 5 |
| 198 | 2 | — | 1 | 1 | 2 | 5 | 5 | 4 | 5 | 5 | 5 | 4 | 5 | 3 |
| 199 | 1 | 2 | 2 | 0 | 1 | 5 | 5 | 2 | 5 | 2 | 5 | 5 | 5 | 5 |
| 200 | 1 | 0 | 1 | 1 | 1 | 5 | 5 | 5 | 5 | 4 | 5 | 4 | 5 | 5 |
| 215 | 0 | 0 | 1 | 0 | 0 | 5 | 5 | — | 4 | — | 3 | 4 | 5 | 5 |
| 216 | 0 | 0 | 0 | 0 | 0 | 5 | 4 | 3 | 5 | — | 2 | 5 | 5 | 3 |
| 217 | 0 | 0 | 1 | 0 | 0 | 5 | 5 | — | 5 | 2 | 4 | 5 | 5 | 5 |
| 284 | 2 | 2 | 1 | 2 | 2 | 5 | 5 | 5 | 5 | 5 | 5 | 4 | 5 | 5 |
| 315 | 2 | 1 | 1 | 1 | 1 | 5 | 5 | 4 | 5 | 5 | 5 | 4 | 5 | 5 |
| 316 | 0 | 0 | 0 | 0 | 0 | 5 | 5 | — | 5 | 4 | 4 | 5 | 5 | 5 |
| 317 | 2 | 1 | 0 | 1 | 1 | 5 | 5 | 3 | 5 | 5 | 5 | 5 | 5 | 5 |
| 318 | 0 | 0 | 0 | 0 | 0 | 5 | 2 | — | 4 | 2 | 4 | 5 | 5 | 5 |
| 334 | 0 | 0 | 1 | 2 | 1 | 3 | 5 | 3 | 5 | 4 | 4 | 2 | 5 | — |
| 339 | 1 | 1 | 0 | 1 | 1 | 4 | 5 | 3 | 5 | 3 | 5 | 4 | 5 | 4 |
| 340 | 2 | 0 | 0 | 1 | 3 | 5 | 5 | 4 | 5 | 4 | 5 | 5 | 5 | 5 |
| 392 | 1 | 0 | 0 | 0 | 5 | 2 | 5 | 2 | 5 | — | 4 | 3 | 5 | — |
| 396 | 2 | 2 | — | 2 | 3 | 5 | 5 | 5 | 5 | 5 | 5 | 5 | 5 | 5 |
| 432 | 0 | 0 | 0 | 0 | 2 | 5 | 5 | 4 | 5 | 3 | 5 | 3 | 5 | 2 |
| 441 | 0 | 0 | 0 | 1 | 1 | 5 | 5 | 5 | 5 | 3 | 5 | 4 | 5 | 1 |
| 447 | 2 | 0 | 0 | 1 | 1 | 5 | 5 | 4 | 5 | 5 | 5 | 3 | 5 | 2 |
| 450 | 2 | 1 | 2 | 1 | 2 | 5 | 5 | 5 | 5 | 5 | 5 | 4 | 5 | 5 |
| 471 | — | 2 | 1 | 1 | 3 | 5 | 5 | 5 | 5 | 5 | 5 | 5 | 5 | 5 |
| 474 | 2 | 2 | 1 | 1 | 1 | 5 | 5 | 5 | 5 | 5 | 5 | 5 | 5 | 5 |
| 476 | 0 | 0 | 0 | 0 | 0 | 3 | 3 | — | 4 | — | 4 | 3 | 5 | 2 |
| 481 | 0 | 0 | 0 | 0 | 0 | 3 | 5 | — | 4 | — | 2 | 2 | 4 | 3 |
| 484 | 1 | 0 | 0 | 0 | 0 | 5 | 5 | — | 5 | — | 5 | 5 | 5 | 5 |
| 487 | 0 | 0 | 0 | 0 | 0 | 5 | 5 | 2 | 3 | — | 4 | 4 | 5 | 3 |
| 488 | 0 | 0 | 1 | 0 | 0 | 5 | 5 | 2 | 5 | — | 5 | 4 | 5 | 5 |
| 489 | 1 | 0 | 0 | 0 | 0 | 5 | 2 | — | 4 | — | 5 | 4 | 5 | 3 |
| 493 | 2 | 2 | 1 | 2 | 2 | 5 | 5 | 4 | 5 | 4 | 5 | 4 | 5 | 5 |
| 494 | 1 | 0 | 0 | 1 | 1 | 5 | 5 | 4 | 5 | 5 | 5 | 4 | 5 | 3 |
| 496 | 0 | 0 | 1 | 1 | 1 | 5 | 5 | 3 | 5 | 5 | 5 | 5 | 5 | 5 |
| 497 | 1 | 1 | 1 | 1 | 1 | 5 | 5 | — | 5 | — | 4 | 5 | 5 | 3 |
| 498 | 0 | 1 | 1 | 1 | 1 | 5 | 5 | 3 | 5 | 4 | 5 | 5 | 5 | 3 |
| 503 | 2 | 1 | 1 | 2 | 2 | 5 | 5 | 5 | 5 | 5 | 5 | 5 | 5 | 5 |
| 507 | 0 | 0 | 0 | 0 | 0 | 0 | — | — | 3 | — | — | 5 | 5 | — |
| 508 | 0 | 0 | 0 | 0 | 0 | 4 | 4 | — | 5 | — | 2 | 3 | 5 | 3 |
| 509 | 0 | 0 | 0 | 0 | 0 | 5 | 2 | — | 3 | — | — | 5 | 5 | 3 |
| 513 | — | 2 | 2 | 2 | 2 | 5 | 5 | 4 | 5 | 3 | 5 | 5 | 5 | 5 |
| 517 | 0 | 0 | 0 | 0 | 0 | 5 | 3 | 3 | 4 | — | — | 3 | 5 | 3 |
| 527 | 2 | 1 | 0 | 1 | 1 | 5 | 5 | 4 | 5 | 4 | 5 | 5 | 5 | 5 |
| 529 | 1 | 1 | — | — | 1 | 5 | 5 | 5 | 5 | 5 | 5 | 5 | 5 | 5 |
| 530 | 1 | 1 | — | 2 | 2 | 5 | 5 | 5 | 5 | 4 | 5 | 5 | 5 | 5 |
| 532 | 1 | 1 | 1 | 2 | 1 | 5 | 5 | 5 | 5 | 5 | 5 | 5 | 5 | 5 |
| 533 | 0 | 0 | 0 | 1 | 0 | 5 | 5 | 3 | 5 | 4 | 4 | 5 | 5 | 5 |
| 534 | 2 | 2 | — | 1 | 1 | 5 | 5 | 4 | 5 | 4 | 5 | 5 | 5 | 5 |

(3) Foliar Spread Test for Upland Field

Wagner pots, each having an area of 1/5000 are, were packed with volcanic ash soil and then each seed of corn, soybean, cotton, wheat, solgum, sugar beat, Large crabgrass, barnyardgrass, green foxtail, blackgrass, annual bluegrass, common lambsquartes, livid amaranth, velvetleaf and morning glory was planted, covered with soil and grown in a glass house at an average temperature of 250° C. for about 2 weeks.

Each wettable powder of the desired compounds (I) shown in Table 1 prepared in accordance with Example 2 was diluted to 500 ppm with water containing a surfactant (0.5%) and then uniformly sprayed on the above respective plants.

After these plants were controlled in a glass house at an average temperature of 25° C. for 3 weeks, the herbicidal effects thereof were investigated.

The herbicidal effects were evaluated according to the evaluation method described in the above (1).

As a result, all compounds (1) showed a bleaching effect. The degree of these effects is shown in Table 6.

TABLE 6

| Compound | Corn | Soybean | Cotton | Wheat | Solgum | Sugar beat | Large crabgrass | Barnyard grass | Green foxtail | Blackgrass | Annual bluegrass | Common lambsquarters | Livid amaranth | Velvetleaf | Morning glory |
|---|---|---|---|---|---|---|---|---|---|---|---|---|---|---|---|
| 86 | 1 | 2 | 1 | 1 | 0 | 2 | 2 | — | 2 | 1 | 1 | 2 | 3 | 1 | 3 |
| 93 | 2 | 4 | 3 | 2 | 1 | 4 | 3 | 2 | 3 | 1 | 1 | 4 | 4 | 2 | 3 |
| 101 | 1 | 3 | 2 | 1 | 1 | 2 | 2 | 1 | 2 | 1 | 1 | 4 | 4 | 3 | 3 |
| 119 | 2 | 2 | 1 | 1 | 1 | 3 | 1 | 1 | 1 | — | — | 4 | 4 | 2 | 3 |
| 120 | 3 | 5 | 2 | 2 | 2 | 5 | 1 | 1 | 3 | 2 | 1 | 4 | 5 | — | 5 |
| 137 | 2 | 3 | 2 | 1 | 1 | 5 | 1 | — | 3 | — | — | — | 4 | 1 | 2 |
| 139 | 3 | 5 | 3 | 2 | 2 | — | 2 | 2 | 4 | 2 | 3 | 5 | 5 | 3 | 5 |
| 140 | 3 | 3 | 3 | 2 | 2 | 3 | 2 | 2 | 2 | 2 | 2 | 4 | 4 | 2 | 3 |
| 141 | 2 | 4 | 3 | 2 | 1 | — | 4 | 4 | 4 | 4 | 4 | 4 | 4 | 4 | 4 |
| 142 | 3 | 4 | 3 | 3 | 2 | 3 | 3 | 2 | 2 | 2 | 3 | 4 | 4 | 3 | 3 |
| 165 | 2 | 5 | 3 | 2 | 2 | — | 3 | 2 | 4 | 3 | 2 | 3 | 4 | 3 | 4 |
| 166 | 3 | 4 | 2 | 1 | 1 | 4 | 3 | 1 | 3 | 1 | — | 4 | 4 | 2 | 4 |
| 171 | 2 | 3 | 4 | 2 | 2 | 3 | 3 | 1 | 5 | 1 | 3 | 4 | 5 | 3 | 5 |
| 177 | 2 | 5 | 3 | 2 | 2 | — | 2 | 2 | 5 | 2 | 4 | 4 | 5 | 4 | 5 |
| 178 | 2 | 3 | 3 | 2 | 2 | 3 | 3 | 2 | 2 | 2 | 3 | 4 | 4 | 3 | — |
| 190 | 2 | 5 | 3 | 2 | 3 | 3 | 3 | 3 | 5 | 3 | 4 | 4 | 5 | 4 | 3 |
| 192 | 2 | 3 | 3 | 2 | 2 | 4 | 3 | 2 | 5 | 2 | 4 | 4 | 4 | 3 | 2 |
| 197 | 4 | 5 | 3 | 2 | 2 | — | 3 | 1 | 5 | 4 | 2 | 4 | 4 | 3 | 4 |
| 199 | 2 | 4 | 3 | 1 | 1 | 3 | 2 | 2 | 2 | 2 | 2 | 4 | 4 | 4 | 4 |
| 200 | 2 | 3 | 3 | 2 | 2 | 4 | 3 | 2 | 5 | 2 | 4 | 4 | 4 | 2 | 3 |
| 284 | 3 | 5 | 3 | 2 | 3 | 4 | 4 | 1 | 4 | 2 | 3 | 4 | 5 | 2 | 3 |
| 315 | 1 | — | — | 2 | 2 | 5 | 2 | — | 5 | 2 | 2 | 5 | 5 | 4 | 3 |
| 316 | 2 | — | — | 1 | 1 | 5 | — | — | 5 | — | — | 3 | 5 | 3 | 2 |
| 317 | 2 | — | — | 2 | 1 | 5 | — | — | 5 | 2 | 5 | 5 | 5 | 3 | — |
| 318 | 1 | 2 | — | 1 | 1 | 5 | — | — | 5 | — | — | 3 | 5 | 2 | — |
| 339 | 2 | 3 | 3 | 1 | 1 | 3 | 3 | 2 | 2 | 2 | 2 | 4 | 4 | 2 | 2 |
| 340 | 2 | 3 | 3 | 2 | 2 | 3 | 4 | 2 | 4 | 2 | 3 | 4 | 4 | 4 | 3 |
| 438 | 2 | 4 | 3 | 2 | 2 | 5 | 3 | 1 | 3 | 2 | 3 | 3 | 5 | 3 | 4 |
| 441 | 2 | 3 | 3 | 2 | 2 | 4 | 2 | 2 | 3 | 2 | 1 | 3 | 3 | — | 1 |
| 447 | 3 | 5 | 4 | 2 | 3 | 5 | 3 | 1 | 2 | 2 | 2 | 5 | 5 | 2 | 5 |
| 450 | 3 | 4 | 5 | 2 | 3 | 5 | 4 | 3 | 3 | 3 | 4 | 4 | 4 | 3 | 2 |
| 457 | 1 | 3 | 3 | 2 | 2 | 3 | 2 | 2 | 3 | 2 | 2 | 3 | 4 | 3 | 3 |
| 471 | 2 | — | — | 2 | 3 | 5 | 5 | — | 5 | 3 | 3 | 5 | 5 | 3 | 5 |
| 474 | 2 | — | — | 2 | 2 | 5 | 5 | — | 5 | 2 | 3 | 5 | 5 | 2 | 5 |
| 476 | 1 | — | — | 1 | 0 | 5 | — | — | — | — | — | 5 | 5 | 2 | — |
| 488 | 1 | 2 | — | 1 | 1 | 5 | — | — | — | — | — | 3 | 5 | 3 | 2 |
| 489 | 1 | — | — | 1 | 1 | 5 | — | — | — | — | — | 5 | 5 | 3 | — |
| 490 | 1 | — | — | 1 | 1 | 4 | — | — | — | — | — | 5 | 4 | 4 | — |
| 491 | 1 | — | 2 | 1 | 1 | 4 | — | — | 2 | — | — | 5 | 4 | 3 | 3 |
| 492 | 1 | — | — | 1 | 1 | 4 | — | — | 2 | — | — | — | 4 | 3 | — |
| 493 | 2 | — | 2 | 1 | 1 | 5 | 2 | — | 5 | — | — | 5 | 5 | 2 | — |
| 494 | 2 | — | 2 | 1 | 1 | 3 | — | — | 3 | — | — | 4 | 5 | 2 | 2 |
| 496 | 2 | — | — | 2 | 2 | 5 | 3 | — | 4 | 3 | 2 | 5 | 5 | 3 | — |
| 497 | 2 | — | 2 | 2 | 1 | 5 | 2 | — | 4 | — | 2 | 2 | 5 | 3 | — |
| 498 | 1 | — | — | 2 | 1 | 4 | 3 | — | 4 | — | 2 | — | 4 | 2 | — |
| 503 | 2 | — | — | 2 | 2 | 4 | 3 | — | 5 | — | 3 | 5 | 5 | 3 | — |
| 513 | — | — | — | — | 3 | 5 | 5 | 3 | 5 | 5 | 5 | 5 | 5 | 5 | 3 |
| 518 | 0 | 0 | 0 | 0 | 0 | 5 | 2 | — | 5 | 2 | — | 2 | 2 | 3 | — |
| 527 | — | — | — | 2 | 1 | 5 | 2 | — | 5 | 2 | 5 | 5 | 5 | 3 | — |
| 529 | — | — | — | 2 | 3 | 5 | 4 | 3 | 5 | 4 | 4 | 5 | 5 | 3 | 3 |
| 530 | — | — | — | 2 | 3 | 5 | 5 | 2 | 5 | 4 | 3 | 5 | 5 | 3 | 3 |
| 532 | 2 | — | — | — | 2 | 5 | 4 | 2 | 5 | 4 | 4 | 5 | 5 | 3 | 3 |
| 533 | 2 | — | — | 2 | 2 | 5 | 3 | 2 | 4 | 3 | 4 | 4 | 5 | 2 | 5 |
| 534 | 2 | — | — | 2 | 2 | 5 | 2 | 2 | — | 3 | 4 | 4 | 5 | 5 | 5 |

UTILIZABILITY IN INDUSTRY

The herbicide containing the benzoxazole compound of the present invention as an effective ingredient has an excellent herbicidal effect.

What is claimed is:

1. A benzoxazole compound represented by the following formula (1):

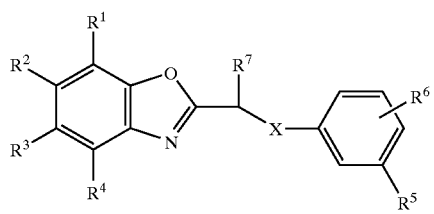

wherein $R^1$ to $R^4$ each represents a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group, a carboxyl group, an alkoxycarbonyl group having 2 to 5 carbon atoms, $R^8S(O)_n$ or $R^9NH$ group; $R^8$ represents an alkyl group having 1 to 6 carbon atoms; n is an integer of 0 to 2; $R^9$ represents a hydrogen atom, an alkyl group having 1 to 4 carbon atoms, an alkylcarbonyl group having 2 to 4 carbon atoms, or a trifluoromethylcarbonyl group; $R^5$ represents a hydrogen atom, an alkyl group having 1 to 6 carbon atoms, an alkoxy group having 1 to 4 carbon atoms, a haloalkyl group having 1 to 4 carbon atoms, a haloalkoxy group having 1 to 4 carbon atoms, a halogen atom, a nitro group, a cyano group or $R^8S(O)_n$; $R^8$ has the same meaning as defined above; $R^6$ represents a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms; $R^7$ represents an alkyl group having 1 to 6 carbon atoms, a haloalkyl group having 1 to 4 carbon atoms or a phenyl group; and X represents O.

2. The benzoxazole compound according to claim 1, wherein $R^1$ to $R^4$ each represents a hydrogen atom, an alkyl group having 1 to 3 carbon atoms, an alkoxy group having 1 to 3 carbon atoms, a haloalkyl group having a fluorine atom, a chlorine atom, a bromine atom or an iodine atom, and having 1 to 3 carbon atoms, a haloalkoxy group having a fluorine atom, a chlorine atom, a bromine atom or an iodine atom, and having 1 to 3 carbon atoms, a chlorine atom, a nitro group, a cyano group, a carboxyl group, an alkoxycarbonyl group having 2 to 4 carbon atoms, $R^8S(O)_n$ or $R^9NH$ group; $R^8$ represents an alkyl group having 1 to 3 carbon atoms; n is an integer of 0 or 2; $R^9$ represents a hydrogen atom, an alkyl group having 1 to 3 carbon atoms, an alkylcarbonyl group having 2 to 3 carbon atoms, or a trifluoromethylcarbonyl group; $R^5$ represents an alkyl group having 1 to 3 carbon atoms, an alkoxy group having 1 to 3 carbon atoms, a haloalkyl group having a fluorine atom, a chlorine atom, a bromine atom or an iodine atom and having 1 to 3 carbon atoms, a haloalkoxy group having a fluorine atom, a chlorine atom, a bromine atom or an iodine atom and having 1 to 3 carbon atoms, a halogen atom, a nitro group, a cyano group or $R^8S(O)_n$; $R^8$ has the same meaning as defined above; $R^6$ represents a hydrogen atom, an alkyl group having 1 to 3 carbon atoms, an alkoxy group having 1 to 3 carbon atoms, a halogen atom, a cyano group, a nitro group or a haloalkyl group having a fluorine atom, a chlorine atom, a bromine atom or an iodine atom and having 1 to 3 carbon atoms; $R^7$ represents an alkyl group having 1 to 3 carbon atoms, a haloalkyl group having a fluorine atom, a chlorine atom, a bromine atom or an iodine atom and having 1 to 3 carbon atoms or a phenyl group.

3. A process for preparing the compound (1) represented by the formula (1) as defined in claim 1, which comprises reacting a compound (4) represented by the following formula (4):

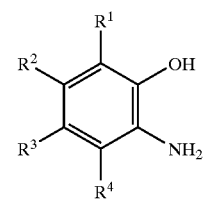

wherein $R^1$ to $R^4$ have the same meanings as defined in claim 1, with a compound represented by the following formula (5):

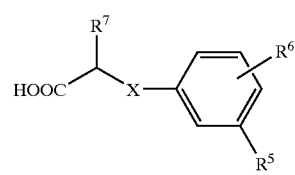

wherein $R^5$ to $R^7$ and X have the same meanings as defined in claim 1, or a reactive derivative thereof.

4. A herbicide composition comprising as an effective ingredient a compound represented by the following formula (1):

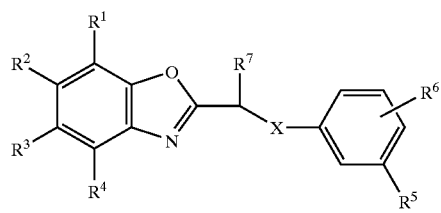

atoms, a haloalkoxy group having 1 to 4 carbon atoms, a halogen atom, a nitro group, a cyano group or $R^8S(O)_n$; $R^8$ has the same meaning as defined above; $R^6$ represents a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms; $R^7$ represents an alkyl group having 1 to 6 carbon atoms, a haloalkyl group having 1 to 4 carbon atoms or a phenyl group; and X represents O.

5. The herbicide composition according to claim 4, wherein $R^1$ to $R^4$ each represents a hydrogen atom, an alkyl group having 1 to 3 carbon atoms, an alkoxy group having 1 to 3 carbon atoms, a haloalkyl group having a fluorine atom, a chlorine atom, a bromine atom or an iodine atom, and having 1 to 3 carbon atoms, a haloalkoxy group having a fluorine atom, a chlorine atom, a bromine atom or an iodine atom, and having 1 to 3 carbon atoms, a chlorine atom, a nitro group, a cyano group, a carboxyl group, an alkoxycarbonyl group having 2 to 4 carbon atoms, $R^8S(O)_n$ or $R^9NH$ group; $R^8$ represents an alkyl group having 1 to 3 carbon atoms; n is an integer of 0 or 2; $R^9$ represents a hydrogen atom, an alkyl group having 1 to 3 carbon atoms, an alkylcarbonyl group having 2 to 3 carbon atoms, or a trifluoromethylcarbonyl group; $R^5$ represents a hydrogen atom, an alkyl group having 1 to 3 carbon atoms, an alkoxy group having 1 to 3 carbon atoms, a haloalkyl group having a fluorine atom, a chlorine atom, a bromine atom or an iodine atom and having 1 to 3 carbon atoms, a haloalkoxy group having a fluorine atom, a chlorine atom, a bromine atom or an iodine atom and having 1 to 3 carbon atoms, a halogen atom, a nitro group, a cyano group or $R^8S(O)_n$; $R^8$ has the same meaning as defined above; $R^6$ represents a hydrogen atom, an alkyl group having 1 to 3 carbon atoms, an alkoxy group having 1 to 3 carbon atoms, a halogen atom, a cyano group, a nitro group or a haloalkyl group having a fluorine atom, a chlorine atom, a bromine atom or an iodine atom and having 1 to 3 carbon atoms; $R^7$ represents an alkyl group having 1 to 3 carbon atoms, a haloalkyl group having a fluorine atom, a chlorine atom, a bromine atom or an iodine atom and having 1 to 3 carbon atoms or a phenyl group.

6. The benzoxazole compound according to claim 1, wherein $R^1$ to $R^4$ each represents a hydrogen atom, an alkoxy group having 1 to 4 carbon atoms, a haloalkyl group having 1 to 4 carbon atoms, a haloalkoxy group having 1 to 4 carbon atoms, a halogen atom, a nitro group, a cyano group, a carboxyl group, an alkoxycarbonyl group having 1 to 4 carbon atoms, $R^8S(O)_n$ or $R^9NH$ groups; $R^8$ represents an alkyl group having 1 to 6 carbon atoms; n is an integer of 0 to 2; $R^9$ represents a hydrogen atom, an alkyl group having 1 to 4 carbon atoms or an alkylcarbonyl group having 1 to 4 carbon atoms; $R_5$ represents an alkoxy group having 1 to 4 carbon atoms, a haloalkyl group having 1 to 4 carbon atoms, a haloalkoxy group having 1 to 4 carbon atoms, a halogen atom, a nitro group, a cyano group or $R^8S(O)_n$; $R^8$ has the same meaning as defined above; $R^6$ represents a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms; $R^7$ represents an alkyl group having 1 to 6 carbon atoms, a haloalkyl group having 1 to 4 carbon atoms or a phenyl group; and X represents O.

7. The benzoxazole compound according to claim 1, wherein $R^3$ is a halogen atom or a cyano group.

8. The benzoxazole compound according to claim 1, wherein $R^5$ is a haloalkyl group having 1 to 4 carbon atoms, a halogen atom, a nitro group or a cyano group.

9. The benzoxazole compound according to claim 1, wherein $R^7$ is an alkyl group having 1 to 6 carbon atoms.

10. The herbicide composition according to claim 4, wherein $R^1$ to $R^4$ each represents a hydrogen atom, an alkoxy group having 1 to 4 carbon atoms, a haloalkyl group having 1 to 4 carbon atoms, a haloalkoxy group having 1 to 4 carbon atoms, a halogen atom, a nitro group, a cyano group, a carboxyl group, an alkoxycarbonyl group having 1 to 4 carbon atoms, $R^8S(O)_n$ or $R^9NH$ group; $R^8$ represents an alkyl group having 1 to 6 carbon atoms; n is an integer of 0 to 2; $R^9$ represents a hydrogen atom, an alkyl group having 1 to 4 carbon atoms or an alkylcarbonyl group having 1 to 4 carbon atoms; $R^5$ represents an alkoxy group having 1 to 4 carbon atoms, a haloalkyl group having 1 to 4 carbon atoms, a haloalkoxy group having 1 to 4 carbon atoms, a halogen atom, a nitro group, a cyano group or $R^8S(O)_n$; $R^8$ has the same meaning as defined above; $R^6$ represents a hydrogen atom, an alkyl group having 1 to 6 carbon atoms, an alkoxy group having 1 to 4 carbon atoms, a halogen atom, a cyano group, a nitro group or a haloalkyl group having 1 to 4 carbon atoms; $R^7$ represents an alkyl group having 1 to 6 carbon atoms, a haloalkyl group having 1 to 4 carbon atoms or a phenyl group; and X represents O.

11. The herbicide composition according to claim 4, wherein $R^3$ is a halogen atom or a cyano group.

12. The herbicide composition according to claim 4, wherein $R^5$ is a haloalkyl group having 1 to 4 carbon atoms, a halogen atom, a nitro group or a cyano group.

13. The herbicide composition according to claim 4, wherein $R^7$ is an alkyl group having 1 to 6 carbon atoms.

* * * * *